(12) United States Patent
Brown

(10) Patent No.: US 8,388,993 B2
(45) Date of Patent: *Mar. 5, 2013

(54) HYALURONAN-CHEMOTHERAPEUTIC AGENT FORMULATIONS FOR THE TREATMENT OF COLON CANCER

(75) Inventor: Tracey J. Brown, Melbourne (AU)

(73) Assignee: Alchemia Oncology Pty Limited, Eight Mile Plains (AU)

( * ) Notice: Subject to any disclaimer, the term of this patent is extended or adjusted under 35 U.S.C. 154(b) by 1350 days.

This patent is subject to a terminal disclaimer.

(21) Appl. No.: 11/415,612

(22) Filed: May 1, 2006

(65) Prior Publication Data

US 2006/0263395 A1 Nov. 23, 2006

Related U.S. Application Data

(63) Continuation of application No. 10/088,774, filed as application No. PCT/AU01/00849 on Jul. 13, 2001, now abandoned.

(30) Foreign Application Priority Data

Jul. 14, 2000 (AU) ...................... PQ8795

(51) Int. Cl.
  *A61F 13/00* (2006.01)
(52) U.S. Cl. ........................ 424/422; 424/400
(58) Field of Classification Search ................ 424/422
  See application file for complete search history.

(56) References Cited

U.S. PATENT DOCUMENTS

| | | | |
|---|---|---|---|
| 4,141,973 A * | 2/1979 | Balazs ............................ | 514/54 |
| 4,160,452 A | 7/1979 | Theeuwes | |
| 4,256,108 A | 3/1981 | Theeuwes | |
| 4,265,874 A | 5/1981 | Bonsen et al. | |
| 4,522,811 A | 6/1985 | Eppstein et al. | |
| 4,665,107 A | 5/1987 | Micale | |
| 4,736,024 A | 4/1988 | Della Valle et al. | |
| 4,851,521 A | 7/1989 | della Valle et al. | |
| 4,965,353 A | 10/1990 | della Valle et al. | |
| 5,095,037 A | 3/1992 | Iwamitsu et al. | |
| 5,128,450 A | 7/1992 | Urdal et al. | |
| 5,202,431 A | 4/1993 | della Valle et al. | |
| 5,208,020 A | 5/1993 | Chari et al. | |
| 5,284,656 A | 2/1994 | Platz et al. | |
| 5,416,071 A * | 5/1995 | Igari et al. ......................... | 514/8 |
| 5,442,053 A | 8/1995 | della Valle et al. | |
| 5,475,092 A | 12/1995 | Chari et al. | |
| 5,585,499 A | 12/1996 | Chari et al. | |
| 5,662,895 A | 9/1997 | Welte et al. | |
| 5,676,964 A | 10/1997 | Della Valle et al. | |
| 5,733,891 A * | 3/1998 | Akima et al. .................... | 514/59 |
| 5,744,155 A | 4/1998 | Friedman et al. | |
| 5,756,475 A * | 5/1998 | Inomata et al. .................. | 514/34 |
| 5,756,537 A | 5/1998 | Gill | |
| 5,776,925 A | 7/1998 | Young et al. | |
| 5,827,834 A * | 10/1998 | Falk et al. ........................ | 514/54 |
| 5,830,882 A | 11/1998 | Falk et al. | |
| 5,840,673 A | 11/1998 | Buckbinder et al. | |
| 5,846,545 A | 12/1998 | Chari et al. | |
| 5,847,002 A | 12/1998 | Willoughby et al. | |
| 5,852,002 A | 12/1998 | Falk et al. | |
| 5,968,972 A | 10/1999 | Broder et al. | |
| 5,977,088 A * | 11/1999 | Harper et al. ................... | 514/54 |
| 5,985,850 A | 11/1999 | Falk et al. | |
| 5,985,851 A | 11/1999 | Falk et al. | |
| 6,027,741 A | 2/2000 | Cialdi et al. | |
| 6,069,135 A | 5/2000 | Falk et al. | |
| 6,087,350 A | 7/2000 | Johnson et al. | |
| 6,214,860 B1 | 4/2001 | Sola et al. | |
| 6,232,301 B1 | 5/2001 | Takahashi et al. | |
| 6,242,457 B1 | 6/2001 | Penco et al. | |
| 6,299,900 B1 | 10/2001 | Reed et al. | |
| 6,475,795 B1 | 11/2002 | Turley et al. | |
| 6,552,184 B1 | 4/2003 | Pallado et al. | |
| 6,579,978 B1 | 6/2003 | Renier et al. | |
| 6,620,927 B2 | 9/2003 | Bulpitt et al. | |
| 6,831,172 B1 | 12/2004 | Barbucci et al. | |
| 2002/0015724 A1 | 2/2002 | Yang et al. | |
| 2003/0087877 A1 | 5/2003 | Calias et al. | |
| 2003/0180382 A1 | 9/2003 | Brown et al. | |
| 2005/0042303 A1 | 2/2005 | Brown et al. | |
| 2005/0267069 A1 | 12/2005 | Brown et al. | |
| 2006/0178342 A1 | 8/2006 | Brown et al. | |
| 2007/0148734 A1 | 6/2007 | Chaudhuri et al. | |
| 2008/0063727 A1 | 3/2008 | Kim et al. | |
| 2009/0054537 A1 | 2/2009 | Brown | |
| 2009/0220497 A1 | 9/2009 | Brown et al. | |
| 2009/0306012 A1 | 12/2009 | Brown et al. | |

FOREIGN PATENT DOCUMENTS

| | | |
|---|---|---|
| CA | 612307 A | 1/1961 |
| CA | 1227427 A1 | 9/1987 |
| CA | 2089621 A1 | 8/1994 |
| CA | 2122519 | 10/1995 |
| CA | 2208924 A | 1/1999 |
| CA | 2370003 A1 | 7/2000 |
| EP | 0 138 572 A2 | 4/1985 |
| EP | 0 138 572 A3 | 4/1985 |
| EP | 0 138 572 B1 | 4/1985 |

(Continued)

OTHER PUBLICATIONS

Avis, K.E. (1975). "Parenteral Preparations," Chapter 84 In *Remington's Pharmaceutical Sciences*, 15th Edition, Easton: Mack Publishing Company, pp. 1461-1487.

Bernatchez, S.F. et al. (1994). "Sodium Hyaluronate as a Vehicle for an Improved Tolerance of 5-Fluorouracil Administered Subconjunctivally to Rabbits," *International Journal of Pharmaceutics* 106:161-166.

Canadian Office Action mailed Apr. 15, 2009, for CA Application No. 2,458,856, two pages.

(Continued)

*Primary Examiner* — James Rogers
(74) *Attorney, Agent, or Firm* — Morrison & Foerster LLP

(57) ABSTRACT

The present invention relates to the enhancement of bioavailability of chemotherapeutic agents for the treatment of disease. In particular, the present invention relates to a method of enhancing the bioavailability of a chemotherapeutic agent comprising the step of administering to a subject in need thereof a therapeutically effective amount of hyaluronan.

8 Claims, 14 Drawing Sheets

FOREIGN PATENT DOCUMENTS

| | | |
|---|---|---|
| EP | 0 216 453 A2 | 4/1987 |
| EP | 0 216 453 A3 | 4/1987 |
| EP | 0 216 453 B1 | 4/1987 |
| EP | 0 265 116 B1 | 4/1988 |
| EP | 0 341 745 A1 | 11/1989 |
| EP | 0 341 745 B1 | 11/1989 |
| EP | 0 433 817 B1 | 6/1991 |
| EP | 0626863 A | 12/1994 |
| EP | 1 598 371 A1 | 11/2005 |
| JP | 61000017 | 1/1986 |
| JP | 61-91986 U | 6/1986 |
| JP | 4-504579 A | 8/1992 |
| WO | WO-91/04058 A2 | 4/1991 |
| WO | WO-93/16733 A1 | 9/1993 |
| WO | WO-94/15640 A1 | 7/1994 |
| WO | WO-94/23725 A1 | 10/1994 |
| WO | WO-95/30423 A2 | 11/1995 |
| WO | WO-95/30423 A3 | 11/1995 |
| WO | WO-95/30439 A2 | 11/1995 |
| WO | WO-95/30439 A3 | 11/1995 |
| WO | WO-96/06622 A1 | 3/1996 |
| WO | WO-97/20564 A1 | 6/1997 |
| WO | WO 97/40841 A1 | 11/1997 |
| WO | WO-98/17320 A1 | 4/1998 |
| WO | WO-98/23648 A1 | 6/1998 |
| WO | WO-99/02151 A1 | 1/1999 |
| WO | WO-00/20642 A1 | 4/2000 |
| WO | WO-00/41730 A1 | 7/2000 |
| WO | WO-01/36656 A2 | 5/2001 |
| WO | WO-01/47561 A1 | 7/2001 |
| WO | WO-02/05852 A1 | 1/2002 |
| WO | WO-03/018062 A1 | 3/2003 |
| WO | WO-2004/076491 A1 | 9/2004 |
| WO | WO-2007/012133 A1 | 2/2007 |
| WO | WO-2007/028196 A1 | 3/2007 |

OTHER PUBLICATIONS

Deardorff, D.L. (1975). "Isotonic Solutions," Chapter 79 In *Remington's Pharmaceutical Sciences*, 15$^{th}$ Edition, Easton: Mack Publishing Company, pp. 1405-1412.

European Search Report mailed Sep. 26, 2005, for EP Application No. 01951219.3, four pages.

Final Office Action mailed Oct. 30, 2008, for U.S. Appl. No. 09/889,203, filed Mar. 13, 2002, 13 pages.

Final Office Action mailed May 11, 2009, for U.S. Appl. No. 11/191,407, filed Jul. 27, 2005, 12 pages.

International Search Report dated Jul. 22, 1994, for PCT Application No. PCT/CA94/00207, filed Apr. 15, 1994, three pages.

International Search Report mailed Apr. 14, 2000, for PCT Application No. PCT/AU00/00004, filed Jan. 6, 2000, six pages.

International Search Report mailed Aug. 22, 2001, for PCT Application No. PCT/AU01/00849, filed Jul. 13, 2001, three pages.

International Search Report mailed Oct. 14, 2002, for PCT Application No. PCT/AU02/01160, filed Aug. 27, 2002, three pages.

International Search Report mailed Sep. 22, 2006, for PCT Application No. PCT/AU2006/001059, filed Jul. 27, 2006, eight pages.

International Search Report mailed Oct. 17, 2006, for PCT Application No. PCT/AU2006/001293, filed Sep. 4, 2006, three pages.

Izawa, O.N. et al. (May 11, 1992). "Hyaluronic Acid Derivative Synthesis and Properties (II)—Synthesis of Hyaluronic Acid Derivative with Thymine 5FU," *41$^{st}$ Society of Polymer Science Japan Conference Proceedings, Polymer Preprints*, Japan, May 26-29, 1992, 42(3):479. (with English translation, eight pages).

Japanese Office Action mailed Jul. 7, 2009, for JP Application No. 2003-522577, with English translation, five pages.

Klein, E.S. et al. (1994). "Effects of Hyaluronic Acid on Experimental Tumor Uptake of 5-Flurouracil," *Reg. Cancer Treat.* 7:163-164.

Langer, R. (Sep. 28, 1990). "New Methods of Drug Delivery," *Science* 249:1527-1533.

Luo, Y. et al. (1999, e-pub. Jul. 27, 1999). "Synthesis and Selective Cytotoxicity of Hyaluronic Acid-Antitumor Bioconjugate," *Bioconjugate Chemistry* 10:755-763.

Maucher, A. et al. (1994). "Antitumor Activity of Coumarin and 7-Hydroxycoumarin Against 7,12-dimethylbenz[a]anthracene-Induced Rat Mammary Carcinomas," *J. Cancer Res. Clin. Oncol.* 120:502-504.

Non-Final Office Action mailed Jun. 11, 2009, for U.S. Appl. No. 11/198,663, filed Aug. 5, 2005, 14 pages.

O'Neil, M.J. et al. eds. (2001). Definition of Irinotecan, Entry 5108, *The Merck Index*, Thirteenth Edition, Merck & Co., Inc.: Whitehouse Station, NJ, p. 915.

Ouchi, T. et al. (1991). "Design of Polysaccharide-5-Fluorouracil Conjugates Exhibiting Antitumour Activities," Chapter 8 *In American Chemical Society Symposium Series*, 469(Polymeric Drugs and Drug Delivery Systems):71-83.

Reynolds, J.E.F. ed. (1993). *Martindale: The Extra Pharmacopoeia*, 30$^{th}$ Edition, The Pharmaceutical Press: London, England, pp. 480-482.

Rivory, L.P. et al. (1996). "Conversion of Irinotecan (CPT-11) to Its Active Metabolite, 7-Ethyl-10-hydroxycamptothecin (SN-38), by Human Liver Carboxylesterase," *Biochemical Pharmacology* 52:1103-1111.

Rosenthal, M.A. et al. (2005, e-pub. May 9, 2005). "Phase I and Pharmacokinetic Evaluation of Intravenous Hyaluronic Acid in Combination with Doxorubicin or 5-Fluorouracil," *Chemotherapy* 51:132-141.

Sakurai, K. et al. (1986). Mucopolysaccharide-type Cancer-Metastasis Inhibitor, Japanese Kokai Patent Application No. Sho 61[1986]-17, with English translation, 36 pages.

Taguchi, T. et al. (Jan. 1994). "An Early Phase II Study of CPT-11 (irinotecan hydrochloride) in Patients with Advanced Breast Cancer," *Gan To Kagaku Ryoho* 21(1):83-90. (Abstract Only) one page.

Takasuna, K. et al. (Aug. 15, 1996). "Involvement of β-Glucuronidase in Intestinal Microflora in the Intestinal Toxicity of the Antitumor Camptothecin Derivative Irinotecan Hydrocholoride (CPT-11) in Rats," *Cancer Research* 56:3752-3757.

Turley, E.A. (Mar. 1992). "Hyaluronan and Cell Locomotion," *Cancer and Metastasis Reviews* 11:21-30.

U.S. Appl. No. 09/889,203, filed Jan. 6, 2000, by Brown.

U.S. Appl. No. 12/482,870, filed Jun. 11, 2009, by Brown et al.

Yamamoto, O.H. et al. (May 11, 1992). "Synthesis of the Conjugate of Adriamycin with Oxidized Hyaluronic Acid," *42$^{nd}$ Society of Polymer Science Japan Annual Conference Proceedings, Polymer Preprints*, Japan, May 31-Jun. 2, 1993, 42(3):898. (with English translation, eight pages).

Yomota, C. (Jul. 3, 1997). "Research for Property Evaluation and Application of Hyaluronic Acid as a Biomedical Polymer," *1996 Human Science Fundamental Research Enterprise, Human Science Enterprise*, 16 pages (with English translation, 32 pages).

Anonymous. (1957). "British Standard Methods for the Determination of the Viscosity of Liquids in C.G.S. Units," *British Standards Institution*, British Standards House, London, 4 pages.

Anonymous. (Jul. 2008). "Sodium Hyaluronate," *European Pharmacopoeia* 62:3835-3837.

Barrow, G.M. (1979). *Physical Chemistry, Fourth Edition*, Jackson, D.C. eds., McGraw-Hill Kogakusha, Ltd., Tokyo, Japan, pp. 764-765.

Bucci, L.R. et al. (2004). "Will the Real Hyaluronan Please Stand Up?" *Journal of Applied Nutrition* 54(1):10-33.

Cunningham, D. et al. (Jul. 22, 2004). "Cetuximab Monotherapy and Cetuximab Plus Irinotecan in Irinotecan-Refractory Metastatic Colorectal Cancer," *New England Journal of Medicine*, download from <http://www.nejm.org>, last visited on Sep. 30, 2010, 351(4):337-345.

Final Office Action mailed Mar. 12, 2010, for U.S. Appl. No. 11/198,663, filed Aug. 5, 2005, 14 pages.

Final Office Action mailed Jun. 30, 2010, for U.S. Appl. No. 11/198,663, filed Aug. 5, 2005, 10 pages.

Hokputsa, S. et al. (2003). "Hydrodynamic Characterisation of Chemically Degraded Hyaluronic Acid," *Carbohydrate Polymers* 52:111-117.

Non-Final Office Action mailed Mar. 25, 2010, for U.S. Appl. No. 09/889,203, filed Mar. 12, 2002, 11 pages.

Non-Final Office Action mailed Oct. 8, 2010, for U.S. Appl. No. 12/065,945, filed Sep. 29, 2008, 13 pages.

Non-Final Office Action mailed, Nov. 15, 2010, for U.S. Appl. No. 11/191,407, filed Jul. 27, 2005, 12 pages.

Stern, R. et al. (2006). "Hyaluronan Fragments: An Information-Rich System," *European Journal of Cell Biology* 85:699-715.

Wikipedia. (download on Sep. 13, 2010). "Intrinsic Viscosity," located at <http://en.wikipedia.org/wiki/Intrinsic_viscosity>, 3 pages.

Wikipedia. (download on Sep. 13, 2010). "Mark-Houwink Equation," located at <http://en.wikipedia.org/wiki/Mark%E2%80%93Houwink_equation>, 2 pages.

Wikipedia. (downloaded on Sep. 13, 2010). "Viscosity," located at <http://en.wikipedia.org/wiki/Viscosity>, 18 pages.

Zhen, Y. et al. (eds). (Nov. 2002). *Modern Biotechnological Pharmaceutics Series*, Antibody Engineering Pharmaceutics, Chemical Industry Press et al., Beijing, China, pp. 303-302, with Certified English Translation, for a total of 10 pages.

Final Office Action mailed Nov. 29, 2010, for U.S. Appl. No. 09/889,203, filed Mar. 13, 2002, 9 pages.

Gustafson, S. et al. (1995). "Studies on Receptors for Hyaluronan and the Turnover of Radioactively-Labelled Hyaluronan in Mice and Rats," *Second International Workshop on Hyaluronan in Drug Delivery, Round Table Series*, Willoughby, D.A. ed., Ontario, Canada, 36:5-7.

Mürdter, T.E. et al. (Jun. 15, 1997, e-published Jun. 1, 1997). "Enhanced Uptake of Doxorubicin into Bronchial Carcinoma: β-Glucuronidase Mediates Release of Doxorubicin froma Glucuronide Prodrug (HMR 1826) at the Tumor Site," *Cancer Research* 57:2440-2445.

Tsatas, D. et al. (2002). "EGF Receptor Modifies Cellular Responses to Hyaluronan in Glioblastoma Cells Lines," *Journal of Clinical Neuroscience* 9(3):282-288.

Non-Final Office Action mailed Apr. 15, 2011, for U.S. Appl. No. 11/996,733, Internationally filed Jul. 27, 2006, 31 pages.

Final Office Action mailed May 2, 2011, for U.S. Appl. No. 11/191,407, filed Jul. 27, 2005, 13 pages.

\* cited by examiner

IC$_{50}$ Drug exposed 3 days:58nM
IC$_{50}$ HA/drug exposed 3 days: 15nM
IC$_{50}$ drug 1h, drug-free 3 days:>100nM
IC$_{50}$ HA/Drug 1h, drug-free 3 days:>100nM Figure represent Mean ± SD, n=4

All figures represent Mean ± SD, n=4

IC$_{50}$ exposed drug 3 days: 46nM
IC$_{50}$ 30min HA, drug 3 days:15nM
IC$_{50}$ 30min HA, Drug 1h: 30nM n=8 where each data point is mean ± SEM

HYALURONAN-CHEMOTHERAPEUTIC AGENT FORMULATIONS FOR THE TREATMENT OF COLON CANCER

FIELD OF THE INVENTION

The present invention relates to the enhancement of bioavailability of chemotherapeutic agents for the treatment of disease. In particular the present invention relates to the use of hyaluronan either alone or in combination with a chemotherapeutic agent to enhancement the bioavailability of the chemotherapeutic agent for treatment of disease. The present invention also relates to the treatment of a drug resistant disease whereby the drug resistance is overcome or alleviated with the use of hyaluronan either alone or in combination with a chemotherapeutic agent.

BACKGROUND TO THE INVENTION

Many diseases that afflict animals, including humans, are treated with chemotherapeutic agents. For example, chemotherapeutic agents have proven valuable in the treatment of neoplastic disorders including connective or autoimmune diseases, metabolic disorders, and dermatological diseases, and many of these agents are highly effective and do not suffer from any bioavailability problems.

Proper use of chemotherapeutic agents requires a thorough familiarity with the natural history and pathophysiology of the disease before selecting the chemotherapeutic agent, determining a dose, and undertaking therapy. Each subject must be carefully evaluated, with attention directed toward factors which may potentiate toxicity, such as overt or occult infections, bleeding dyscrasias, poor nutritional status, and severe metabolic disturbances. In addition, the functional condition of certain major organs, such as liver, kidneys, and bone marrow, is extremely important. Therefore, the selection of the appropriate chemotherapeutic agent and devising an effective therapeutic regimen is influenced by the presentation of the subject. Such considerations affect the dosage and type of drug administered.

Unfortunately, not all chemotherapeutics are readily useable. For example, some chemotherapeutic agents are inherently refractory in that animal cells do not readily respond to these agents, while other chemotherapeutics suffer from acquired resistance. For instance, it is well recognised that some subjects on prolonged chemotherapy are forced to change chemotherapeutics as these become less efficacious with time. Moreover, some chemotherapeutics, while not affected by inherent or acquired resistance per se, are not effective in the treatment of certain diseases as they have innate problems with bioavailability. One disease that is frequently affected by both cellular resistance and bioavailability problems is cancer.

Cancer is responsible for one in four deaths in Western society. While the rates of new cases of cancer and deaths with cancer decreased in the United States and Canada between 1990-1994, the data show that 2,604,650 people in the United States died from cancer between 1990-1994, with more men (53%) than women (47%) affected. The most common cancer deaths were due to cancer of the lung (728,641), colon and rectum (285,724), breast (218,786), and prostate (169,943).

Among women, the most common cancers are breast (31%), lung (12%), colon and rectum (12%), uterus (6%), and ovary (4%), with breast and ovarian cancer representing approximately 35% of all cancers found in women. The majority of women diagnosed with these forms of cancer receive a combination of surgical, radiation therapy or chemotherapy.

Chemotherapeutic agents used to treat cancer can be subdivided into several broad categories, including, (1) alkylating agents, such as mechlorethamine, cyclophosphamide, melphalan, uracil mustard, chlorambucil, busulfan, carmustine, lomustine, semustine, streptozoticin, and decrabazine; (2) antimetabolites, such as methotrexate, fluorouracil, fluorodeoxyuridine, cytarabine, azarabine, idoxuridine, mercaptopurine, azathioprine, thioguanine, and adenine arabinoside; (3) natural product derivatives, such as vinblastine, vincristine, dactinomycin, daunorubicin, doxorubicin, mithramycin, taxanes (e.g., paclitaxel) bleomycin, etoposide, teniposide, and mitomycin C; and (4) miscellaneous agents, such as hydroxyurea, procarbezine, mititane, and cisplatinum.

Important cancer chemotherapeutic agents (with the usual effective dosage) to which clinical multidrug-resistance has been observed include vinblastine (0.1 mg per kilogram per week), vincristine (0.01 mg per kilogram per week), etoposide (35 to 50 mg per square meter per day), dactinomycin (0.15 mg per kilogram per day), doxorubicin (500 to 600 mg per square meter per week), daunorubicin (65 to 75 mg per square meter per week), and mithramycin (0.025 mg per kilogram per day).

It is well appreciated by those skilled in the field that, at present, there are no effective means of overcoming cellular resistance to chemotherapeutic agents. More importantly there are no practical means of increasing bioavailability of chemotherapeutics without concomitant increase in toxicity or side effects. Accordingly, there is a requirement for means of overcoming or at least alleviating the problems associated with acquired or inherent cellular resistance as well as means of increasing bioavailability of chemotherapeutics.

The applicant has previously investigated the usefulness of hyaluronan (HA) as a drug delivery vehicle for chemotherapeutics, and found that HA was useful when co-administered with these drugs. International patent application no. PCT/AU00/00004 was filed covering this invention, and is incorporated in its entirety herein by reference. HA, also known as hyaluronic acid, is a naturally occurring polysaccharide comprising linear-chain polymers, which is found ubiquitously throughout the animal kingdom. HA is highly water-soluble, making it an ideal drug delivery vehicle for biological systems.

Subsequent to the filing of International patent application no. PCT/AU00/00004, the applicant surprising found that HA could act as a sole agent. It was found that HA could exert a cytotoxic effect on human breast cancer cells, as well as pre-sensitizing cells so that they became more susceptible to chemotherapeutic agents. The present invention therefore provides methods whereby cells that were, or had become resistant to chemotherapeutic agents could be effectively treated. More importantly, by using the disclosed methods it is possible to decrease the dosages of chemotherapeutic agents without decreasing the efficacy to the subject. The methods of the invention include administering hyaluronan either alone in conjunction with a chemotherapeutic agent.

The present invention is based upon the discovery that hyaluronan, derivatives, analogues, and salts thereof, not only inhibit cells per se, but also allows the safe administration of selected chemotherapeutic agents at standard or lower doses thought to be less effective, to treat subjects including human subjects. In vivo administration of hyaluronan in combination with chemotherapeutic agents also enhances the therapeutic effect of these agents against cells that are refractory, thus preventing the subsequent emergence of multidrug resistance.

Diseased cells such as cancer cells often have more permeable membranes due to an alteration in the membrane potential, or increased receptor status which can alter the regulation of their intracellular molecule transport which can result in cell swelling (Lang et al, 1993). While the applicant does not wish to be bound by any theory they postulate that there are several mechanisms that could explain the cellular effect that HA is exerting both as a sole agent, and as a pre-treatment for therapeutic agents:

1). When HA is bound to CD44, RHAMM and the scavenger receptor bound, the nett negative charge of HA alters the membrane potential of the cell resulting in an increase in cell permeability consequently enabling a greater flux of drug into the diseases cell.

2). When HA is bound to diseased cells such as tumour cells and internalised there could be a hyperosmotic effect resulting in cell lysis.

3). HA could exert oxidative membrane damage resulting in apoptosis.

4). HA internalisation could elevate the mitochondrial membrane potential which could result in cell death or increased drug retention.

Since HA is administered at satuarable levels, there would be a constant internalisation of the glycosaminoglycan which means that any therapeutic agent which is in an equilibrium within the volumetric domain of the HA is co-internalised resulting in a concentrated intracellular release of the drug

SUMMARY OF INVENTION

In its broadest aspect the present invention provides a method of treating a subject in need thereof comprising the step of administering to said subject a therapeutically effective amount of hyaluronan in conjunction with a chemotherapeutic agent such that said chemotherapeutic agent is more effective than when administered alone.

The present invention also provides a method of enhancing the bioavailability of a chemotherapeutic agent comprising the step of administering to a subject in need thereof a therapeutically effective amount of hyaluronan.

Hyaluronan can be used to significantly enhance the bioavailability of any administered chemotherapeutic agent. Preferably, the chemotherapeutic agent that is administered is selected from the group consisting of carmustine (BCNU), chlorambucil (Leukeran), cisplatin (Platinol), Cytarabine, doxorubicin (Adriamycin), fluorouracil (5-FU), methoxetrate (Mexate), CPT111, etoposide, plicamycin (Mithracin) and taxanes such as, for example, paclitaxel.

In yet another embodiment, the invention provides a method of treating or preventing multidrug resistance or drug-resistant cells comprising the step of administering a therapeutically effective amount of hyaluronan, prior to, together with, or subsequent to the administration of a chemotherapeutic agent.

As described more fully below, administration of hyaluronan and a chemotherapeutic agent results in the suppression of tumor growth by at least 50%; preferably 60%; and, more preferably, greater than 70%. Accordingly, the elimination of tumor growth and proliferation eliminates the production of multidrug resistant cells reducing the recurrence of cancer and increasing the efficacy of chemotherapeutic treatments.

The present invention further provides a pharmaceutical composition for increasing the sensitivity of cells to chemotherapeutic agents comprising hyaluronan. The hyaluronan and/or chemotherapeutic agent may also be administered together with a further pharmaceutical carrier.

The present invention also provides a method of treating cancer cells comprising the step of administering to a patient in thereof a therapeutically effective amount of hyaluronan.

Typically said cancer cells are resistant to chemotherapeutic drugs.

In a further aspect of the present invention there is provided a method of overcoming cellular resistance, comprising the step of administering a therapeutically effective amount of HA.

Throughout the description and claims of this specification, the word "comprise" and variations of the word, such as "comprising" and "comprises", means "including but not limited to" and is not intended to exclude other additives, components, integers or steps.

DETAILED DESCRIPTION OF THE INVENTION

Figure 1:
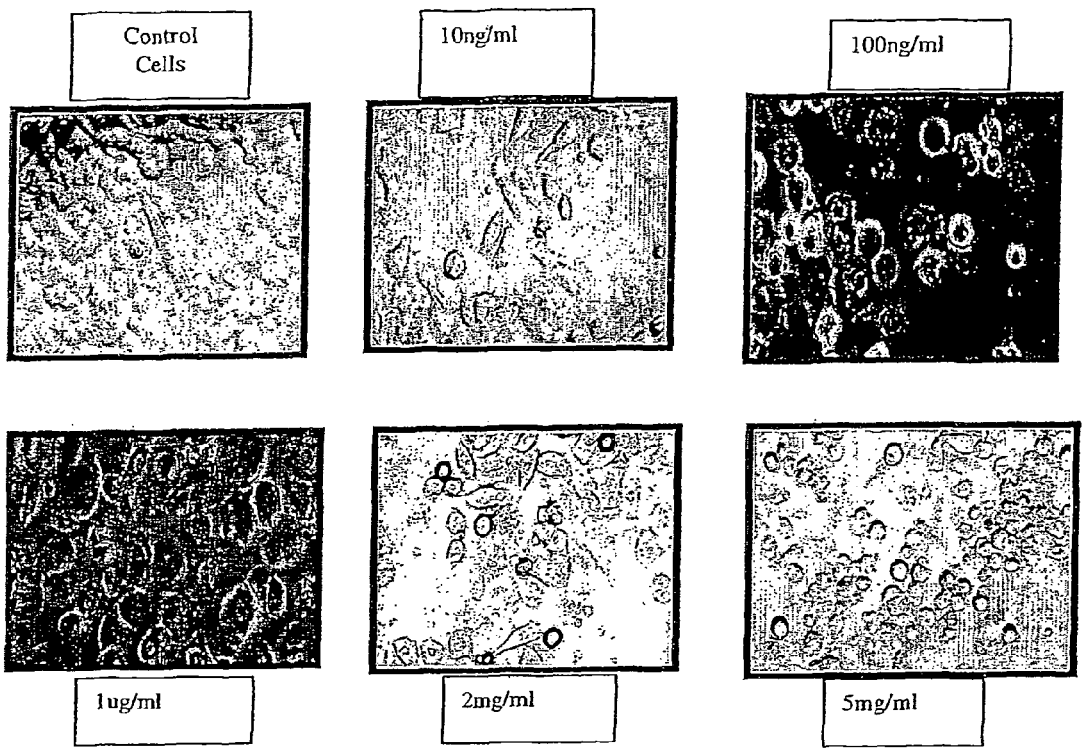
FIG. 1 shows exponentially growing breast cancer cells exposed to 750,000 dalton HA for 24 h at which stage the cells were photographed. At 10 ng/ml there was a reduction in cell number, but no difference in morphology was noted. At 100 ng/ml and 1 µg/ml the cells appeared top be undergoing a osmotic response where the cells appeared to swell. At 2 mg/ml and 5 mg/ml the cells became granular and the plasma membrane was "pitted" possibly indicating an osmotic response and/or the commencement of cell death.
Figure 2A:
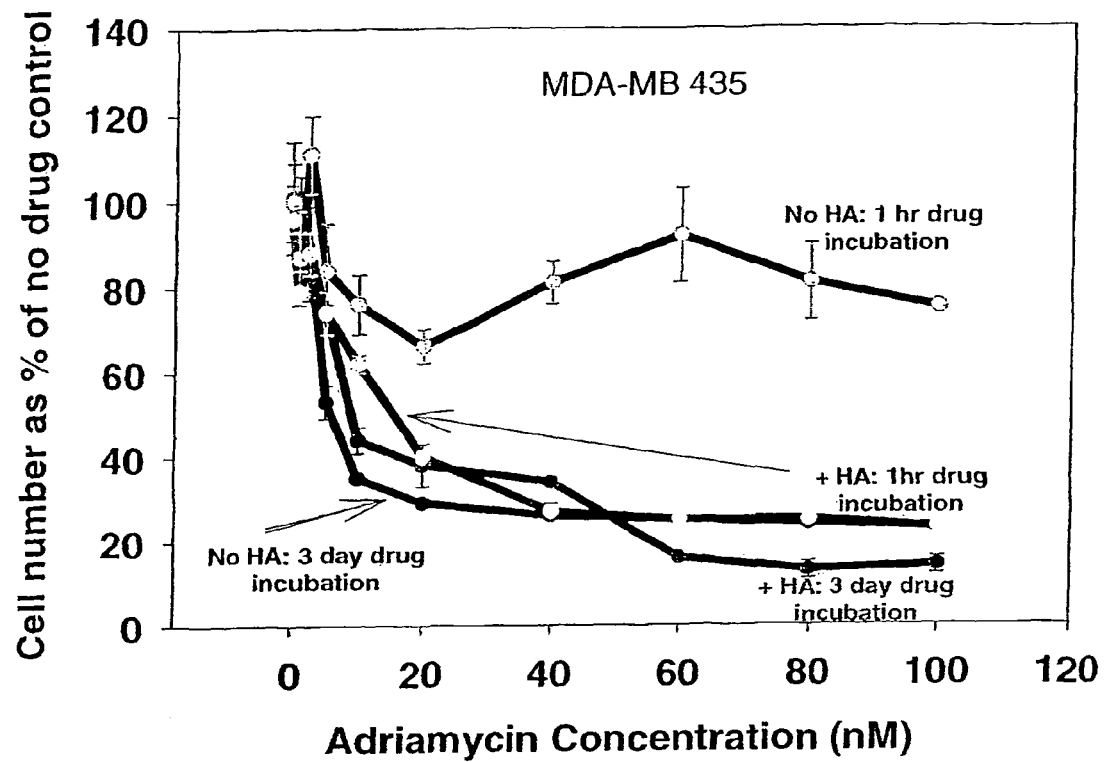
FIG. 2a-2f shows exponentially growing breast cancer cells that were exposed to 750,000 dalton HA for 30 min, 1 h, or 24 h at which stage the cells were varying concentrations of adriamycin. These figures also illustrate the effect of HA/drug co-incubation for the period of 1 or 3 days. These diagrams illustrate that HA can "pre-sensitise" and/or chemosensitise cells to therapeutic drugs.
Figure 2B:
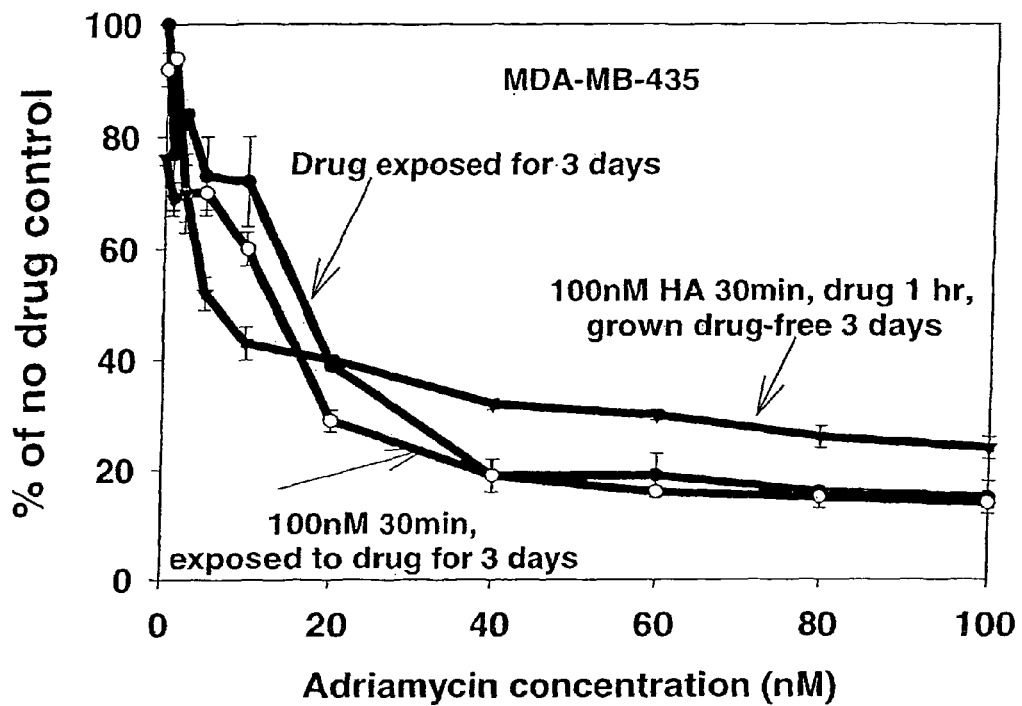
Figure 2C:
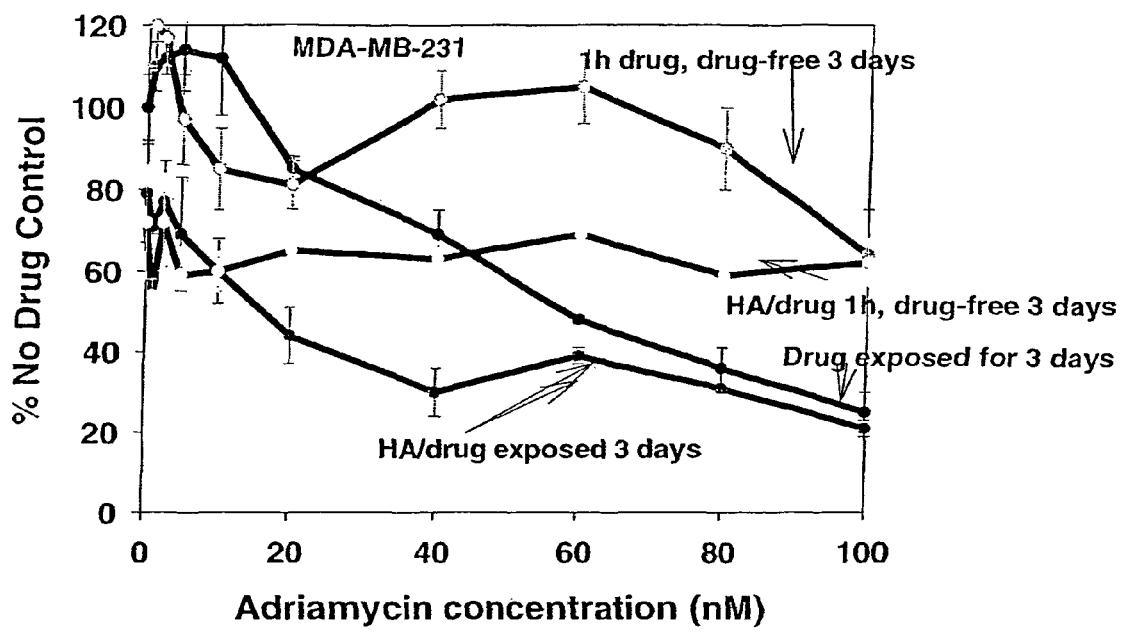
Figure 2D:
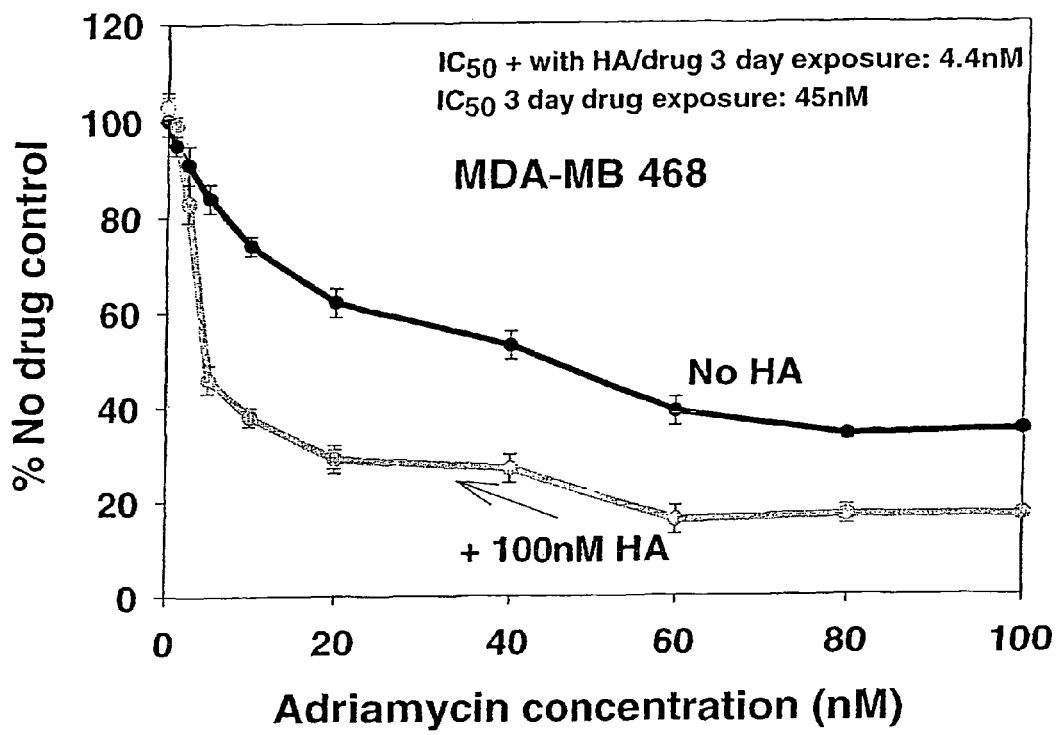
Figure 2E:
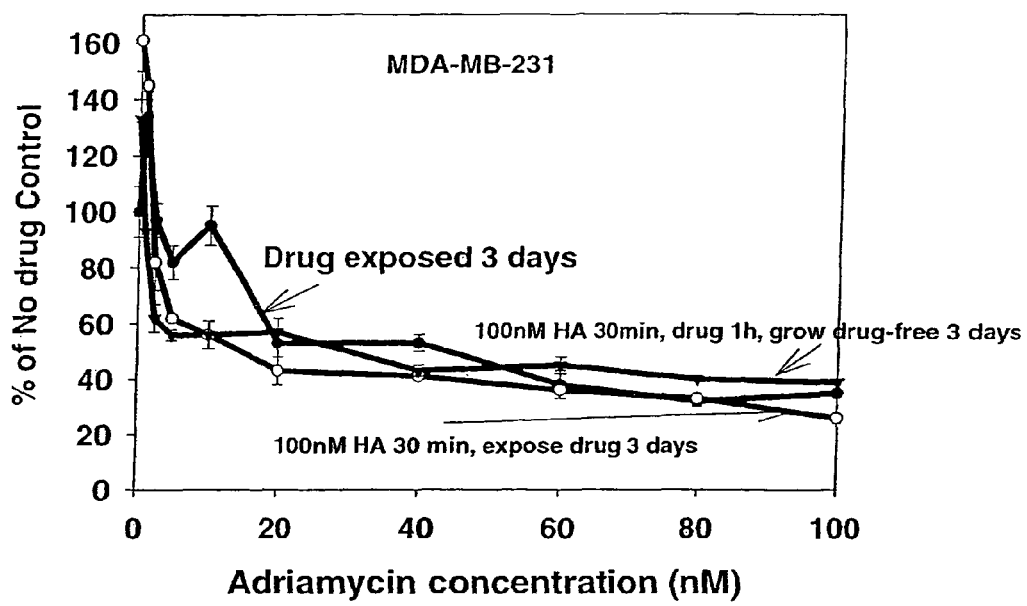
Figure 2F:
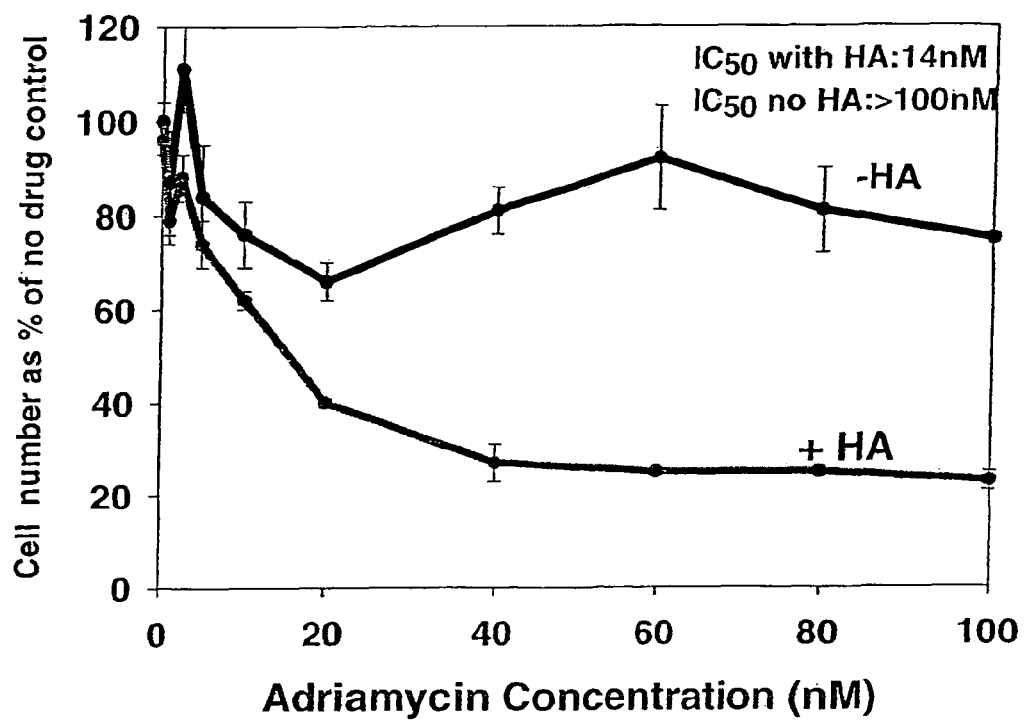
Figure 3A:
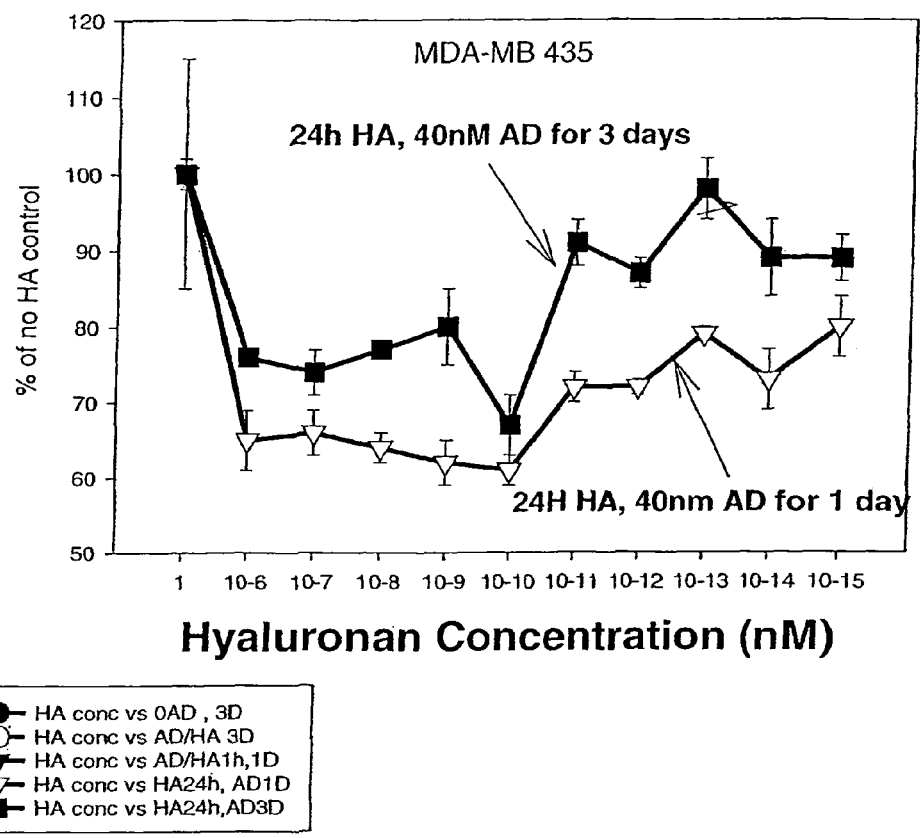
FIGS. 3a-3d shows exponentially growing breast cancer cells exposed to varying concentrations of 750,000 dalton hyaluronan for 1 h, 24 h or 3 days followed by treatment with 40 nM Adriamycin for varying time periods of 1 h, 24 h or 3 days. These figures show that a wide concentration range of hyaluronan can act as a chemosenitiser or exert a cytotoxic effect.
Figure 3B:
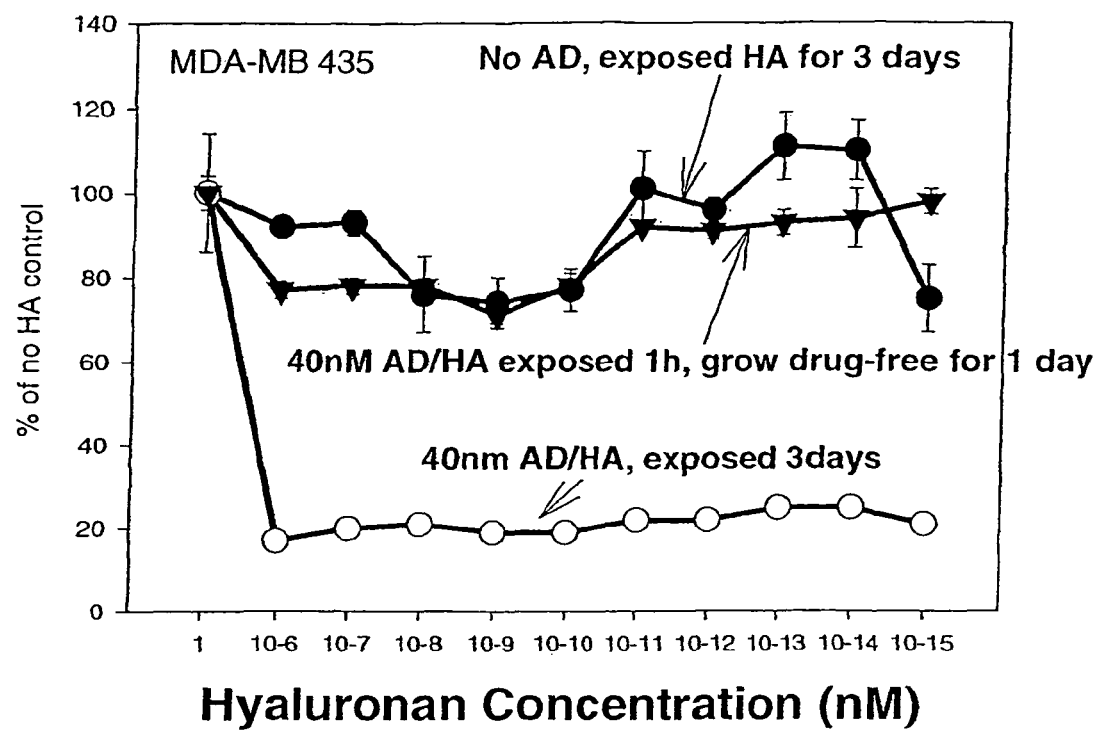
Figure 3C:
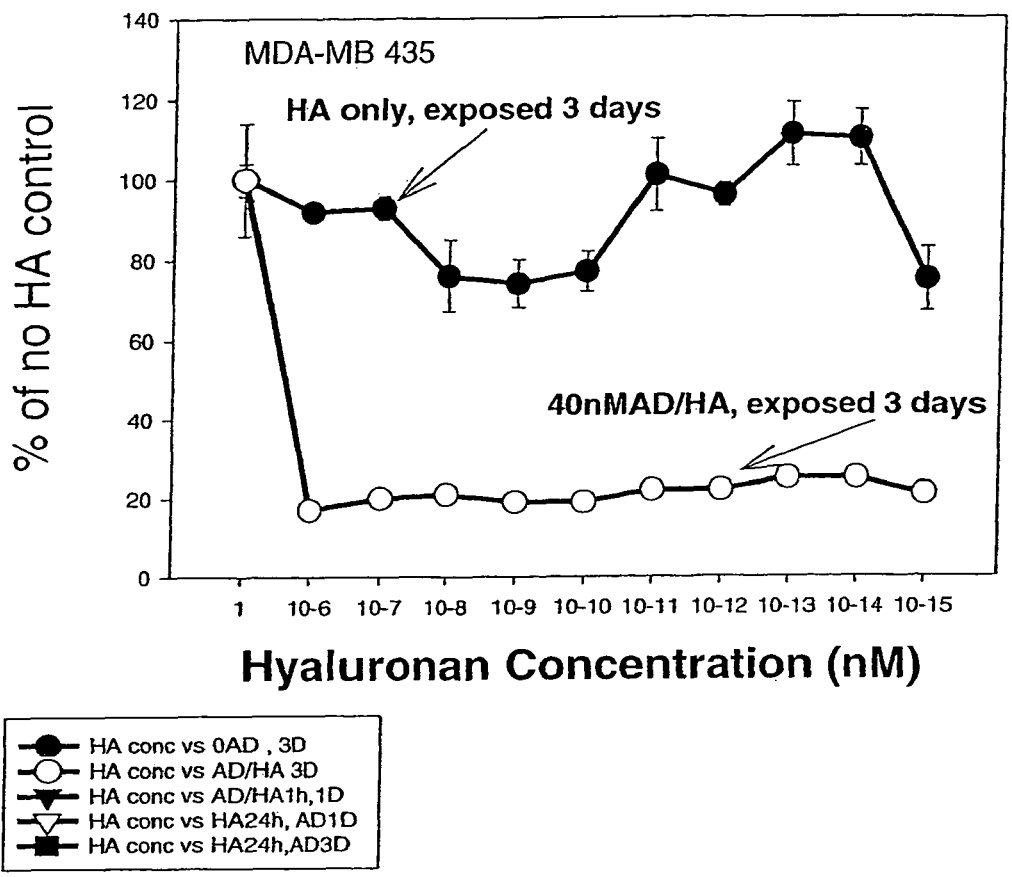
Figure 3D:
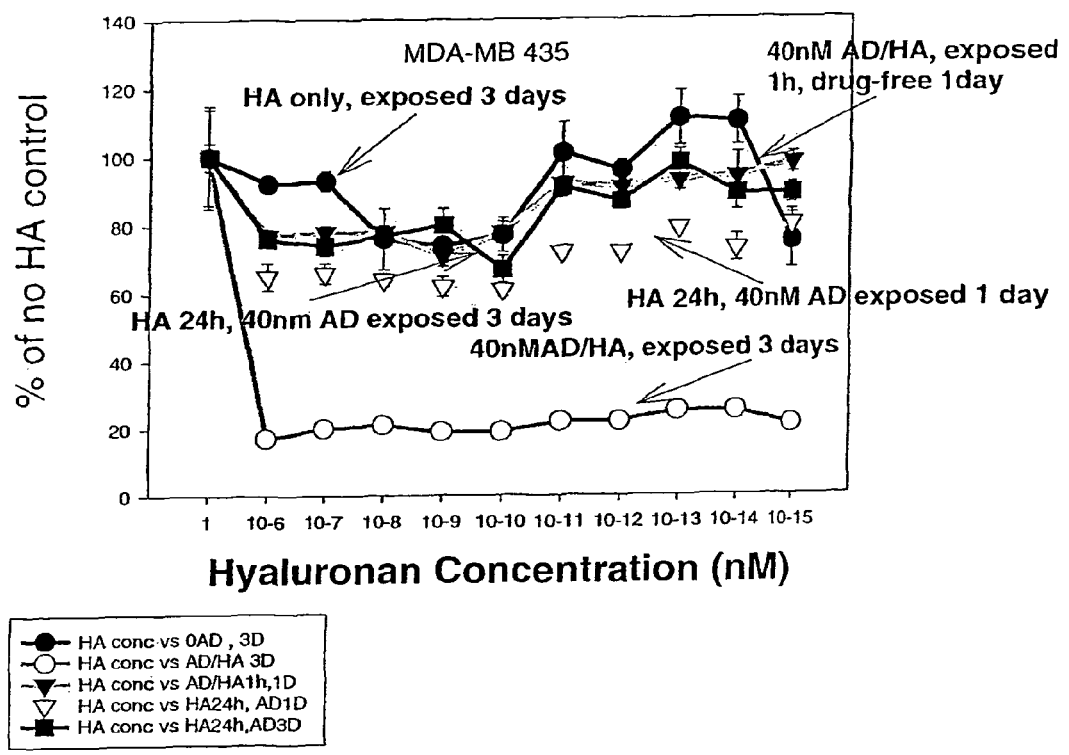

The methods and compositions of the invention are useful for increasing the sensitivity of cells to chemotherapeutic agents such as, for example, anti-cancer agents like paclitaxel, analgesics, opiates, hormones or antibiotics and the like. In particular the methods and compositions of the invention are useful for increasing the sensitivity of cells associated with cellular proliferative disorders (eg., a neoplasm) By increasing the efficacy without concomitant toxicity to non-cancer cells the invention provides methods and compositions useful for treating tumors and preventing or reducing the chances of relapse and death as a result of cytotoxicity. In addition, the invention eliminates or reduces the number of multidrug resistant cells by eliminating cancer cells prior to any mutation inducing a multidrug resistant phenotype. Accordingly, by reducing multi-drug resistant tumor cells from arising, the invention satisfies the shortcomings of current therapeutic modalities.

The term "subject" as used herein refers to any animal having a disease or condition which requires treatment with a chemotherapeutic agent wherein the chemotherapeutic agent has reduced efficacy relative to that desired. Preferably the subject is suffering from a cellular proliferative disorder (eg., a neoplastic disorder). Subjects for the purposes of the invention include, but are not limited to, mammals (eg., bovine, canine, equine, feline, porcine) and preferably humans.

By "cell proliferative disorder" is meant that a cell or cells demonstrate abnormal growth, typically aberrant growth, leading to a neoplasm, tumor or a cancer.

Cell proliferative disorders include, for example, cancers of the breast, lung, prostate, kidney, skin, neural, ovary, uterus, liver, pancreas, epithelial, gastric, intestinal, exocrine, endocrine, lymphatic, haematopoietic system or head and neck tissue.

Generally, neoplastic diseases are conditions in which abnormal proliferation of cells results in a mass of tissue called a neoplasm or tumor. Neoplasms have varying degrees of abnormalities in structure and behaviour. Some neoplasms are benign while others are malignant or cancerous. An effective treatment of neoplastic disease would be considered a valuable contribution to the search for cancer preventive or curative procedures.

The methods of this invention involve in one embodiment, (1) the administration of hyaluronan, prior to, together with, or subsequent to the administration of a chemotherapeutic agent; or (2) the administration of a combination of hyaluronan and a chemotherapeutic agent.

As used herein, the term "therapeutically effective amount" is meant an amount of a compound of the present invention effective to yield a desired therapeutic response. For example to prevent cancer or treat the symptoms of cancer in a host or an amount effective to treat cancer.

The specific "therapeutically effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical carrier" is a pharmaceutically acceptable solvent, suspending agent or vehicle for delivering the hyaluronan and/or chemotherapeutic agent to the animal or human. The carrier may be liquid or solid and is selected with the planned manner of administration in mind.

As used herein, "cancer" refers to all types of cancers or neoplasm or malignant tumours found in mammals. Cancer includes sarcomas, lymphomas and other cancers. The following types are examples, but are, but is not intended to be limited to these particular types of cancers: prostate, colon, breast, both the MX-1 and the MCF lines, pancreatic, neuroblastoma, rhabdomysarcoma, home, lung, murine, melanoma, leukemia, pancreatic, melanoma, ovarian, brain, head & neck, kidney, mesothelioma, sarcoma, Kaposi's, sarcoma, stomach, and uterine.

As used herein, the term "cell" include but is not limited to mammalian cells (eg., mouse cells rat cells or human cells).

The hyaluronan and/or chemotherapeutic agents may be administered orally, topically, or parenterally in dosage unit formulations containing conventional non-toxic pharmaceutically acceptable carriers, adjuvants, and vehicles. The term parenteral as used herein includes subcutaneous injections, aerosol, intravenous, intramuscular, intrathecal, intracranial, intrasternal injection or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The hyaluronan as well as the chemotherapeutic agents useful in the method of the invention can be administered, for in vivo application, parenterally by injection or by gradual perfusion over time independently or together. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

It is envisioned that the invention can be used to treat pathologies associated cell proliferative disorders, including, for example, neoplasms, cancers (eg., cancers of the breast, lung, prostate, kidney, skin, neural, ovary, uterus, liver, pancreas, epithelial, gastric, intestinal, exocrine, endocrine, lymphatic, haematopoietic system or head and neck tissue), fibrotic disorders and the like.

The methods and compounds of the invention may also be used to treat other diseases associated with chemotherapeutic treatment such as neurodegenerative disorders, hormonal imbalance and the like. Therefore, the present invention encompasses methods for ameliorating a disorder associated with cell proliferation, neoplasms, cancers and the like, including treating a subject having the disorder, at the site of the disorder, with hyaluronan and a chemotherapeutic agent in an amount sufficient to inhibit or ameliorate the cell's proliferation or the disorder. Generally, the terms "treating", "treatment" and the like are used herein to mean affecting a subject, tissue or cell to obtain a desired pharmacologic and/or physiologic effect. The effect may be prophylactic in terms of completely or partially preventing a cell proliferative disorder or sign or symptom thereof, and/or may be therapeutic in terms of a partial or complete cure for a disorder and/or adverse effect attributable to, for example, aberrant cell proliferation. "Treating" as used herein covers any treatment of, or prevention of a cell proliferative disorder in a vertebrate, a mammal, particularly a human, and includes: (a) preventing the disorder from occurring in a subject that may be predisposed to the disorder, but has not yet been diagnosed as having it; (b) inhibiting the disorder, i.e., arresting its development; or (c) relieving or ameliorating the disorder, i.e., cause regression of the disorder.

The invention includes various pharmaceutical compositions useful for ameliorating cell proliferative disorder, including neoplasms, cancers and the like. The pharmaceutical compositions according to one embodiment of the invention are prepared by bringing hyaluronan, analogue, derivatives or salts thereof and one or more chemotherapeutic agents or combinations of hyaluronan and one or more chemotherapeutic agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, eg., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Hyaluronan together with a chemotherapeutic agent of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compounds of the present invention are of the order of about 0.5 mg to about 10 mg per kilogram body weight, with a preferred dosage range between about 5 mg to about 20 mg per kilogram body weight per day (from about 0.3 gms to about 1.2 gms per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the instant invention may form solvates with water or common organic solvents. Such solvates are encompassed within the scope of the invention.

The compounds of the present invention may additionally be combined with other compounds to provide an operative combination. It is intended to include any chemically compatible combination of chemotherapeutic agents, as long as the combination does not eliminate the activity of the hyaluronan of this invention.

The invention will now be further described by way of reference only to the following non-limiting examples. It should be understood, however, that the examples following are illustrative only, and should not be taken in any way as a restriction on the generality of the invention described above. In particular, while the invention is described in detail in relation to cancer, it will be clearly understood that the findings herein are not limited to treatment of cancer. For example, HA may be used for treatment of other conditions.

EXAMPLE 1

Preparation of Hyaluronan and 5-Fluorouracil Solutions

HA used in all of the in vitro and in vivo studies were obtained from Kyowa Hakko Kogyo (Yamaguchi, Japan). 5-FU was obtained from Sigma, St. Louis, USA. And Adraimycin from Cytomix, Northcote, Melbourne, Australia. A standard profile of the HA used is shown in Table 1.

TABLE 1

Specification Sheet For Hyaluronan Bulk Dried Powder

| TEST | SPECIFICATION |
| --- | --- |
| 1. Description | White or cream coloured powder or granules, odourless |
| 2. Identification (IR Spectrum) | Conforms to Reference Standard |
| 3. pH (1% solution) | 5.0 to 7.0 |
| 4. Loss on Drying | NMT 10.0% |
| 5. Residue on Ignition | 15.0 to 19.0% |
| 6. Protein Content | NMT 0.1% |
| 7. Heavy Metals | NMT 20 ppm |
| 8. Arsenic | NMT 2 ppm |
| 9. Sodium Hyaluronate Assay | 97.0–102.0% (dried basis) |
| 10. Intrinsic Viscosity | 10.0–14.5 dL/g |
| 11. Total Aerobic Microbial Count (USP 23) | NMT 50 CFU/gram |
| 12. *Staphylococcus aureus* (USP 23) | Absent |

TABLE 1-continued

Specification Sheet For Hyaluronan Bulk Dried Powder

| TEST | SPECIFICATION |
| --- | --- |
| 13. *Pseudomonas aeruginosa* (USP 23) | Absent |
| 14. Yeasts and Moulds (USP 23) | NMT 50 CFU/gram |
| 15. Bacterial Endotoxin (LAL) (USP23) | NMT 0.07 EU/mg |

A 10 mg/ml stock of HA solution was prepared by dissolving desiccated HA (modal Mr $7.5 \times 10^5$ kDa) in pyrogen-free injection grade water. To ensure a homogenous solution the HA was dissolved overnight at 4° C. followed by thorough vortexing. To ensure that the HA had maintained its molecular weight during the preparation of the stock solution, the solution was analysed on a Sephacryl S-1000 size exclusion gel with column specifications of 1.6 cm×70 cm, sample size 2 ml, flow rate 18 ml/h and 2 ml fraction size. Hyaluronan was detected in column fractions by the uronic acid assay.

The uronic acid assay was used to detect the presence of hyaluronan qualitatively from the fractions collected from the gel filtration chromatography procedure. A 25 μl aliquot of each fraction was then transferred into a 96 well plate. 250 μl of a carbazole reagent (3M carbazole/0.025M borate in $H_2SO_4$) was then added to these fractions. The 96 well plate was incubated for 45-60 min at 80° C. A Dynatech MR7000 plate reader with a 550 nm filter was used to read the 96 well plate. The absorbance was considered to be significant when it was >3 standard deviations above the background absorbance. The background was calculated by taking an equal number of sample points before and after $V_o$ and $V_t$ where the average number taken was 16 (Fraser et al. 1998).

A stock solution of 5-FU was prepared by dissolving powdered 5-FU in 01M NaOH (pH 8.9) and brought to a concentration of 1 mg/ml with pyrogen-free injection grade 0.9% w/v NaCl. The stock solution was filtered through a 0.22 μm filter to ensure sterility. The 5-FU was diluted by adding the required volume of stock solution to the cell-line specific growth medium as specified above.

A 10 mg/ml solution of adriamycin in 0.9% NaCl was obtained from Cytomix.

EXAMPLE 2

Testing the Effect of Hyaluronan on Cancer Cell Morphology

Human breast adenocarcinoma cell lines MDA-MB-468, MDA-MB-435 and MDA-MB-231 were selected based on HA binding affinity (Culty et al, 1994), and the expression of the HA receptors of CD44 and RHAMM (Wang et al, 1996). The characteristics of these cell lines are shown in Table 2.

TABLE 2

Hyaluronan Binding And Receptor Expression Of Human Mammary Carcinoma Cell Lines

| Cell Line | Type of breast cancer | Degree of HA Binding[a] | HA Receptor Expression[b] | |
| --- | --- | --- | --- | --- |
| | | | CD44 | RHAMM |
| MDA-MB-231 | adenocarcinoma | ++ | +++ | +++ |
| MDA-MB-468 | adenocarcinoma | ++++ | ++++ | ++ |
| MDA-MB-435 | ductal carcinoma | + | +++ | ND |

[a]Culty et al, 1994
[b]Wang et al, 1996

Cell lines MDA-MB-468, MDA-MB-435 and MDA-MB-231 were routinely grown and subcultured as a monolayer in 175 cm² culture flasks in Leibovitz L-15 Medium supplemented with 10% Foetal calf serum (FCS) and antibiotic/antimycotic reagents at 37° C. in humidity controlled incubator with 100% (v/v) air.

Leibovitz-L-15 with glutamine (10× concentrate) RPMI (10× concentrate), Eagles basal medium (EBM, 10× concentrate), 20 mM HEPES, 0.09% w/v bicarbonate, Hanks' Balanced Salt Solution (HBSS, 10× concentrate) and Dulbecco's Phosphate Buffered Saline without calcium and magnesium (PBS, 10× concentrate) were purchased from Sigma (St Louis, Mo., USA). Powder concentrates were dissolved in the required volume of reverse osmosis deionised pyrogen-free distilled water to make a single strength solution, sterilised by 0.22 µm high pressure filtration (Millipore Corporation, MA. U.S.A.), and stored at 4° C. FCS) were purchased from the CSL Ltd., Australia. FCS was stored at −20° C. Antibiotic/antimycotic solution (100× concentrate) containing 10,000 units penicillin, 10 mg streptomycin and 25 µg amphotericin U/ml was obtained from Sigma (St Louis, USA). Trypsin/EDTA solution (10× concentrate) containing 5 g porcine trypsin and 2 g EDTA/L in 0.9% w/v sodium chloride was obtained from Sigma (St Louis, Mo., USA). All breast cancer cell lines were purchased from American tissue culture collection (Rockville, USA). All plastic disposable culture vessels were purchased from Greiner (Austria). Eight-welled, tissue culture microscope slides were obtained from Linbro (Flow Laboratories, VA, USA).

For the tests, MDA MB-468, MDA MB-231 and MDA MB-435 cell line were grown in 90% Leibovitz L-15 medium supplemented with 10% FCS. When confluent the cultures were washed 1× in HBSS and trypsinised in 0.25% trypsin/0.05% EDTA. The cell suspensions were counted with an automated cell counter (ZM-2 Coulter Counter) by adding 15 mL saline+0.2 ml of cell suspension.

Cells were resuspended to a number of:
MDA MB-468: 25,000 cell/ml of media
MDA MB-231: 12,000 cell/ml of media
MDA MB-435: 12,000 cell/ml of media The cells were plated into 48-well plates (1 cm² surface area) by adding 1 ml of cell suspension per well. Cells were allowed to attach for 24 h, before the media was removed, monolayers washed. The test media was: growth media containing 0-1 µM adriamycin or 5-fluorouracil with or without the addition of 0-1 µM of HA (modal Mw 750,000). The cells were exposed to the several combinations of HA and drugs for different times and at different concentrations (Table 3).

TABLE 3

Incubation Conditions for Hyaluronan and Drugs with Human Breast Cancer Cells

| Sequence of HA/Drug Addition | HA Incubation Time | Drug Incubation Time | Growth Time |
|---|---|---|---|
| 0–1 µM HA, media wash, 0–1 µM drug, media wash, grow drug-free | 30 min | 1 h | 1 day |
| 0–1 µM HA, media wash, 0–1 µM drug, media wash, grow drug-free | 1 h | 1 h | 1 day |
| 0–1 µM HA, media wash, 0–1 µM drug, media wash, grow drug-free | 24 h | 1 h | 1 day |
| 0–1 µM HA, media wash, 0–1 µM drug, media wash, grow drug-free | 24 h | 24 | 1 day |

TABLE 3-continued

Incubation Conditions for Hyaluronan and Drugs with Human Breast Cancer Cells

| Sequence of HA/Drug Addition | HA Incubation Time | Drug Incubation Time | Growth Time |
|---|---|---|---|
| 0–1 µM HA, media wash, 0–1 µM drug, media wash, grow drug-free | 30 min | 1 h | 3 day |
| 0–1 µM HA, media wash, 0–1 µM drug, media wash, grow drug-free | 1 h | 1 h | 3 day |
| 0–1 µM HA, media wash, 0–1 µM drug, media wash, grow drug-free | 24 h | 1 h | 3 day |
| 0–1 µM HA, media wash, 0–1 µM drug, media wash, grow drug-free | 24 h | 24 | 3 day |
| 0–1 µM drug/100 nM HA | | 30 min | 1 day |
| 0–1 µM drug/100 nM HA | | 1 h | 1 day |
| 0–1 µM drug/100 nM HA | | 24 | 1 day |
| 0–1 µM drug/100 nM HA | | 30 min | 3 days |
| 0–1 µM drug/100 nM HA | | 1 h | 3 days |
| 0–1 µM drug/100 nM HA | | 24 | 3 days |
| 0–1 µM HA | 30 min | | 1 day |
| 0–1 µM HA | 1 h | | 1 day |
| 0–1 µM HA | 24 | | 1 day |
| 0–1 µM HA | 30 min | | 3 days |
| 0–1 µM HA | 1 h | | 3 days |
| 0–1 µM HA | 24 | | 3 days |
| 0–1 µM HA | 3 days | | 3 days |

After the incubation and growth periods the cell monolayers were washed with HBSS and trypsinised in 0.25% trypsin/0.05% EDTA. The cell suspensions were counted with an automated cell counter (ZM-2 Coulter Counter) by adding 15 mL saline+0.2 ml of cell suspension. Results were expressed as % of no drug control which was calculated as:

$$\frac{\text{Cell count} \times 100}{\text{Cells in no drug control}}$$

Or depending on the experiment as % of drug control, calculated as:

$$\frac{\text{Cell count} \times 100}{\text{Cells in drug control}}$$

Exponentially growing human breast cancer cells MDA MB 231 as described in example 2 were incubated with 0-5 mg/ml HA (modal Mr 750,000 D) for 24 h. At 24 h the cells were counted and photographed with CPR, 1600 film rolls from Eastman Kodak Company, Rochester, USA.

When HA was incubated with breast cancer cells for 30 min, 1 h, 24 h or 3 days a varied response was observed, where the reduction in breast cancer cell number ranged from 0-29% (See Table 4).

TABLE 4

Cytotoxic Effect of HA on Human Breast Cancer Cell Lines

| Exposure Time | Cell Line MDA-MB 468 | Cell Line MDA-MB 231 | Cell Line MDA-MB 435 |
|---|---|---|---|
| 3 days 100 nM | −29% | −23% | −22% |

TABLE 4-continued

Cytotoxic Effect of HA on Human Breast Cancer Cell Lines

| Exposure Time | Cell Line MDA-MB 468 | Cell Line MDA-MB 231 | Cell Line MDA-MB 435 |
|---|---|---|---|
| 1 h 100 nM | +3% | −21% | −4% |
| 30 min 100 nM | −5% | −27% | −12% |
| 30 min 500 nM | −22% | | 0 |
| 30 min 1000 nM | +2% | −26% | ND |
| 24 h 100 nM | −5% | −8% | −12% |

*Figures are the mean of 2–3 separate determinations

When human breast cancer cells were incubated with HA specific morphological changes (See FIG. 1) were also observed such as swelling of the plasma membrane, greater granularity of cytosolic components.

When human breast cancer cells were exposed to HA for 30 min, 1 h, 24 h or 3 days followed by exposure toadriamycin, it became evident that HA ehanced the cytotoxicity of the drug (FIG. 3 & Table 5).

TABLE 5

Effect of HA on Adriamycin Cytotoxicity in Breast Cancer Cell Lines

| Treatment | $IC_{50}$ MDA-MB 468 | $IC_{50}$ MDA-MB 231 | $IC_{50}$ MDA-MB 435 |
|---|---|---|---|
| 3 day drug exposure | 3 to 12 | 4 to 5 | 10 |
| 1 h drug/HA, 3 days drug-free | 40 | 2 to 8 | 0 |
| 1 h drug, 3 days drug-free | 20 to 40 | 3 to 9 | 6 to 10 |
| 30 min 100 nm HA, 1 hr drug, 3 days drug-free | 2 to 20 | 2 to 6 | 4 to 40 |
| 30 min 100 nM HA, 3 day drug exposure | 3 to 18 | 2 to 4 | 2 to 8 |
| 30 min 500 nM HA, 3 day drug exposure | 3 to 9 | 2 to 8 | 2 to 4 |
| 30 min 1000 nM HA, 3 day drug exposure | 1 to 10 | 2 to 8 | 1 to 5 |
| 24 h 100 nM HA, 3 day drug exposure | 8 to 12 | 13 | 24 |
| 24 h 100 nM HA, 1 h drug exposure, drug-free 3 days | 50 to 60 | 9 | 21 |

All figures represent the range of 2-3 separate experiments, where the numerical values are the multiplication factor decrease in $IC_{50}$ which is exerted by the addition of HA to drug or pre-sensitization of cancer cells with HA before the addition of drug.

EXAMPLE 3

Efficacy of Hyaluronan In Vivo

Based on the results from the in vitro drug sensitivity experiments in Example 2, evaluation of the treatment efficacy of hyaluronan as a sole agent, and as a chemosensitizer in the treatment human breast carcinomas in vivo was undertaken.

From the results in Example 2 the carcinoma cell line MDA-MB-468 was selected as the cancer cell inoculant for the generation of any nude mouse human tumour xenografts. Cells were routinely grown and subcultured as a previously described in Example 2. For injection into mice, cells were grown to 100% confluency, trypsinised in 0.025% trypsin/0.01% EDTA solution, washed twice by centrifugation in a Beckman TJ-6 bench centrifuge at 400 $g_{av}$ for 10 min, counted using a Model-ZM Coulter counter and resuspended in serum-free Leibovitz L-15 medium at $1\times10^8$ cells/ml.

Six to eight weeks old athymic CBA/WEHI nude female mice, purchased from the Walter and Eliza Hall Research Institute, Melbourne Australia, were maintained under specific pathogen-free conditions, with sterilised food and water available ad libitum. Each mouse received one injection containing $5\times10^6$ cells in 50 μl. The cells were injected with a 26 gauge needle into the mammary fat pad directly under the first nipple (Lamszus et al, 1997). Tumour measurements were made weekly by measuring three perpendicular diameters ($d_1 d_2 d_3$). Tumour volume was estimated using the formula:

$$(\tfrac{1}{6})\pi(d_1 d_2 d_3)$$

Treatment with 5-FU±HA was commenced approximately 4-8 weeks after the cancer cell inoculation. The mean tumour size for mice used in each study is summarised in Table 6.

TABLE 6

Summary of Human Breast Cancer Tumours at Commencement of Each Study

| Study | Tumour volume (mean ± SEM) | Tumour as % of net body mass (mean ± SEM) |
|---|---|---|
| Efficacy: 6-week | $0.37 \pm 0.20$ mm$^3$ | $0.19 \pm 0.10$ mm$^3$ |

Approximately 8 weeks after tumour induction two tumour-bearing mice were given a lethal dose of Nembutal. Within 3 min of killing the mice, tumours were surgically removed and immediately fixed in 10% buffered formalin for 12 h. The fixed tumour was dehydrated overnight in a series of 70-100% ethanol, followed by paraffin embedding from which 2-4 μm sections were cut. The sections were placed on slides, de-waxed, and brought to water. Slides were washed 3×5 min in PBS. Heterophile proteins were blocked by incubation with 10% foetal calf serum for 10 min, followed by a PBS rinse.

Secondary antibodies used in the visualisation of HA and HA synthase antibodies were purchased from Dako (California, U.S.A.). 3,3'-Diaminobenzidine (Sigma Fast DAB) tablets were obtained from Sigma, St. Louis, USA.

The detection antibodies were applied for 60 min at RT. The detection antisera or antibodies were against RHAMM, CD44H and CAE. The slides were washed 3×5 min in PBS and endogenous peroxidase activity blocked by immersion in 0.3% $H_2O_2$ in methanol for 20 min. Following a further PBS wash, the peroxidase-conjugated swine anti-rabbit secondary antiserum was applied for 60 min at RT, followed by 3×5 min washes in PBS. Sigma Fast 3,3'-Diaminobenzidine tablets (DAB) were prepared according to the manufacturer's instructions and the DAB solution was applied for 5-10 min at RT. The slides were washed in tap water for 10 min, counterstained with haematoxylin, dehydrated and mounted.

Individual injections of 5-FU were prepared according to individual mouse masses, with the aim of delivering 30 mg/kg 5-FU in 50 μl (equivalent to human therapeutic dose of 10.5 mg/kg for a mean body weight of 60 kg; Inaba et al, 1988). HA injection comprising a final HA concentration equivalent to 12.5 mg/kg of mouse mass were prepared so that deliver of 12.5 mg/kg HA in 50 μl could be effected. With this quantity of HA injected into the body, saturation kinetics would be observed for the period of the experimentation (Fraser et al, 1983).

One of the most commonly used treatment regimens for human breast cancer is cyclophosphamide, methotrexate and 5-fluorouacil, which is administered on day 1 and 8 of a 28 day cycle In human breast cancer the initial treatment regimen is for 6 cycles at which time the patient condition is re-assessed, therefore we tried to simulate the human treatment regimen as closely as possible by exposing the mice to 6 cycles (6 months) of treatment in a long term efficacy study and a 6 cycles (6 week) short term efficacy study. Considering the life cycle of a mouse is approximately 2 years we commenced both short-term and long-term treatment protocols (see Table 7).

TABLE 7

Treatment Administration Protocols.

| Treatment Group | Dosage | 6-Week Study Treatment Regimen Bolus injection on Days |
|---|---|---|
| 1. Saline | 0.1 ml of 0.9% saline (injection grade) | 1 & 2 of 7 day cycle |
| 2. HA | 0.1 ml containing: 12.5 mg/kg HA | 1 & 2 of 7 day cycle |
| 3. 5-FU | 0.1 ml containing: 30 mg/kg 5-FU | 1 & 2 of 7 day cycle |
| 4. HA followed by 5-FU | 0.1 ml containing: 12.5 mg/kg HA or 30 mg/kg 5-FU | 1: HA<br>2: 5-FU<br>3: HA<br>4: 5-FU<br>of 7 day cycle |
| 5. HA | 0.1 ml containing: 12.5 mg/kg HA | 1: HA<br>3: HA<br>of 7 day cycle |
| 6. 5-FU | 0.1 ml containing: 30 mg/kg 5-FU | 2: HA<br>4: HA<br>of 7 day cycle |

Mice were randomly divided into 7 groups of 8 animals per group for the short term study and 5 groups of 8 animals for the long term study (refer to Table 7 for dosage and treatment administration schedule).

The treatment was not extended over the 6 month regimen since it has been demonstrated that chemotherapy lasting more than six months has not generally been associated with greater benefit (Harris et al, 1992).

Animals were weighed and tumour volumes measured on the day of treatment application for long term study. In the 6-week study animals were weighed and tumour volumes measured on a daily basis. Animals were individually placed in an injection box, and the injections were administered via the tail vein. It has been experimentally proven that stress can be a major factor in a patients response to chemotherapy (Shackney et al, 1978), therefore we ensured that equal numbers of mice were allocated to each cage, the animal number per cage varied from 5-8 depending on the stage of experimentation.

The experimental end-point occurred when the animal had to be euthanised due to degree of disease progression or when the 6 month (long term) or 6 week (short term) treatment regimen was completed. Due to the animal ethics guidelines the animals were monitored fortnightly by an independent animal ethics officer who assessed the degree of disease progression. The following criteria were used to determine if an animal had reached the stage of experimental end-point of necessary death:

1). Tumour mass was so large the animal was immobilised;
2). Animal was not eating or drinking and had experienced dramatic weight loss; or
3). Tumour size was greater than 10% of body mass.

At the experimental end-point the animals were anaesthetized by a 0.1 ml intra-peritoneal injection of Nembutal (60 mg/ml), blood was collected followed by killing of the animals using cervical dislocation.

Immediately after killing the mouse the tumour, liver, heart, spleen, bladder, left and right kidneys, uterus, lungs, stomach, intestines, brain and lymph nodes were excised and placed in 4% formalin buffered with 0.06M phosphate pH 7.5, and cetylpyridinium chloride, 1.0% w/v. The tissue was fixed for 16-24 h before histological processing. Fixed tissue was dehydrated stepwise to 100% ethanol and embedded in paraffin blocks from which 2-4 μm sections were placed on glass microscope slides. Staining the tissue sections with a haematoxylin nuclear stain and eosin cytoplasmic stain highlighted any pathological features that could indicate treatment toxicity.

Nine to 11 lymph nodes were collected per animal, ensuring that all nodes which drained the tumour area were collected. There are currently two methods used for the detection of lymph node metastasis
 i) routine haematoxylin and eosin staining of gross organ structure; and
 ii) immunohistochemistry using a cancer marker such as carcinoembryonic antigen.

Both methods of metastasis detection were employed in this study. Not all commercially available CEA antibodies react with human breast cancer cells, so we tested the reactivity of 5 different antibodies (DAKO, Amersham and KPL).

The haematoxylin and eosin stained lymph nodes were examined by Dr P. Allen (certified pathologist) where each node was microscopically examined for the presence of tumour cells. The CEA immunostained lymph nodes were microscopically examined, where any positively stained nodes were counted and considered positive for lymph node metastasis.

Figure 6:
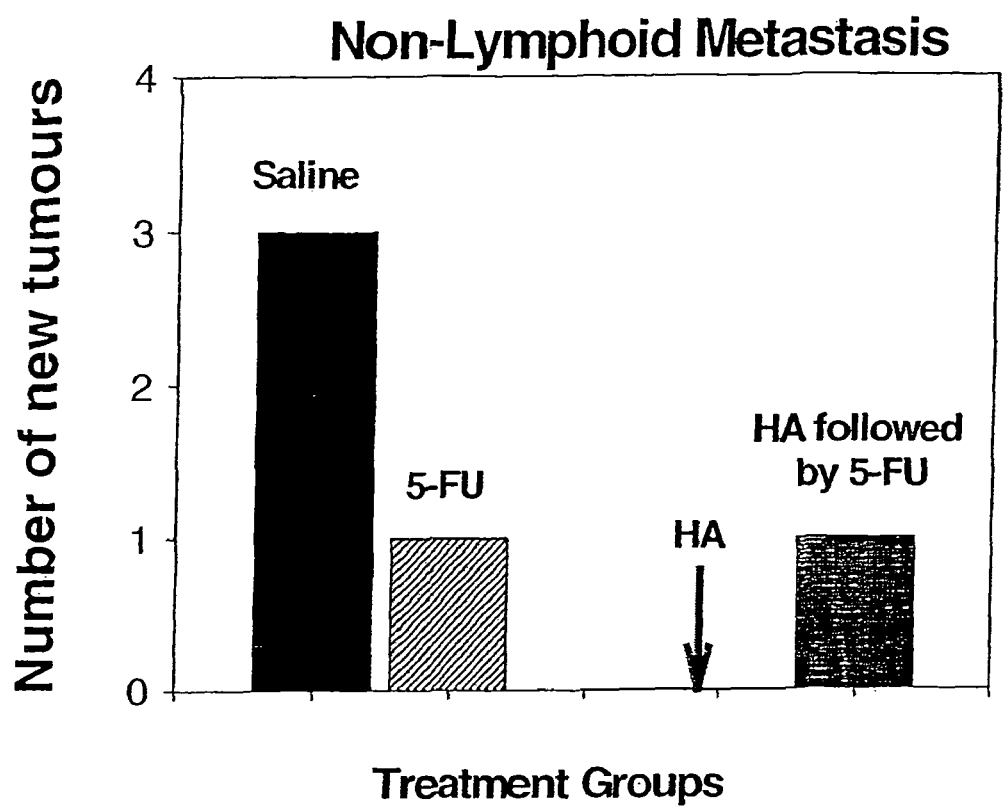
FIG. 6 shows that the co-administration of HA resulted in a significant reduction in non-lymphoid metastasis. With the exception of the mice receiving the HA therapy, new tumours were observed around the neck or underarm region of the area adjacent to the primary tumour.

Tumour volume was monitored on a daily or weekly basis by calliper measurements and tumour volume calculated as previously described. At the end of the 6 week study, tumour mass was determined where the HA chemosensitizing therapy had significantly smaller tumours than the saline group, HA and 5-FU groups (p=0.005) as seen in FIG. 6. No significant differences in tumour response were noted in the initial 2 weeks of treatment, but thereafter the HA followed by 5-FU tumour growth was retarded in comparison to the other treatment groups. During the 6 weeks of treatment interesting differences were noted in the number of tumour doubling cycles. Mice receiving the saline treatment underwent an average of 4 tumour doublings, while the incorporation of HA into the treatment regimen significantly increased the tumour doubling time where HA/5-FU animals underwent an average of one tumour doubling cycle, once again highlighting the effect of HA on 5-FU cytotoxicity.

All animals displayed lymph node metastasis in lymph nodes that were adjacent to the primary tumour. The percentage of lymph node involvement (number of metastatic nodes per animal) was greatly reduced by the HA followed by 5-FU, 5-FU and HA treatment, where the saline group demonstrated a 6-fold increase in the amount of lymph node involvement. The other treatment groups demonstrated a significantly smaller percentage at 12.2-14.3% (Dunnett's Multiple Comparison Test, p=<0.001).

The co-administration of HA resulted in a significant reduction in non-lymphoid metastasis. With the exception of the mice receiving the HA therapy, new tumours were observed around the neck or underarm region of the area adjacent to the primary tumour.

Gastro-Intestinal Tract Toxicity:

One of the most common toxic effects of 5-FU is on the gastro-intestinal tract where haemorrhagic enteritis and intestinal perforation can occur (Martindale, 1993). Animals were monitored daily for GI tract upset such as diarrhoea and weekly for more severe toxicity manifestations such as weight loss. Weight loss was monitored by calculating net body weight as estimated by subtracting tumour weight, which was calculated as 1 g×tumour volume (cm$^3$) as cited in Shibamoto et al, 1996. For demonstration of any weight changes the animal body weight was normalised to the body weight at the time of treatment commencement as $$\frac{\text{Body mass (ex tumour)} - \text{body mass at commencement of treatment (ex tumour)}}{\text{Body mass at commencement of treatment (ex tumour)}} \times 100$$

Figure 4:
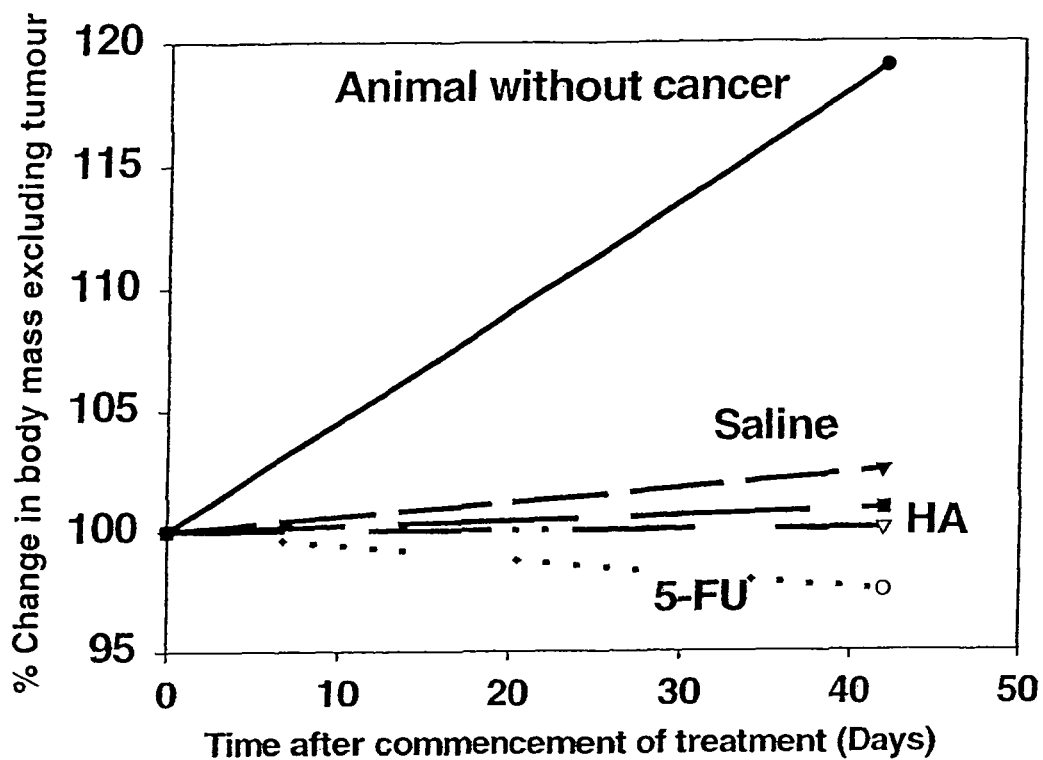
FIG. 4 shows that there was no treatment toxicity noted throughout the 6-week study. In comparison to the 5-FU treatment group the mice receiving HA therapy, that is as a sole agent or as a chemosensitizer, demonstrated enhanced well being where the animal did not loose weight, but maintained its body mass.

No treatment toxicity was noted throughout the 6-week study. In comparison to the 5-FU treatment group the mice receiving HA therapy, that is as a sole agent or as a chemosensitizer, demonstrated enhanced well being where the animal did not loose weight, but maintained its body mass (FIG. 4).

Blood Marrow Suppression

As one of the major toxicities associated with 5-FU treatment is depression of the bone marrow and subsequent drop in white blood cells it was necessary to assess any treatment associated blood toxicity. Upon anaesthetising the animals, blood was collected from the heart or great vessels using a needle and syringe. Estimation of white blood cell number by making a 1/50 dilution of blood in mouse tenacity saline (M) and counting it on a haemocytometer. A differential blood count was performed by counting-neutrophils, lymphocytes, and erythrocytes. The total estimation of blood cell sub-populations was compared to published data for mouse blood.

The total white cell count and sub-population differential were not significantly different, regardless of the treatment.

Effect of Treatment on Organ Mass

To ensure that treatments did not induce organ atrophy or enlargement, the organs were removed and weighed during the post mortem. The mass of each organ was calculated as a % of the overall net body weight, and compared to the organ masses of the saline only group (Group 1).

The overall patient survival time was calculated as the time (days or weeks) that the animal lived after the commencement of treatment. All animals in each treatment group completed the 6-week treatment program.

In relation to organ mass, the HA therapy did not result in any dramatic toxicity. Mice receiving 5-FU exhibited an enlarged spleen (61% increase in mass), while the co-administration of HA and 5-FU significantly counteracted this enlargement by 31% (student t-test, p<0.001). The 5-FU therapy resulted in a shrinkage of the uterus (22%), once again the HA/5-FU therapy reduced this toxic effect by 10% (student t-test, p=0.04). It was also clearly defined that the addition of HA to the treatment regimen, when co-administered or administered the day before, significantly decreased the primary tumour mass in comparison to the saline treatment group (student t-test, p=0.006). No other differences in organ mass were noted between treatments.

EXAMPLE 4

Effect of Hyaluronan Concentration on the In Vitro Efficacy of 5-FU

MDA-MB 468, MDA-MB 435 and MDA-MB 231 cells were cultured as described in Example 2. When the cultures had reached 70-80% confluency they were washed in 1×HBSS at 37° C. and trypsinised in 10 ml of 0.25% trypsin/ 0.05% EDTA until cells have fully detached. After add 1 ml of FCS to neutralise trypsin the cells were counted, centrifuged at 1,200 rpm for 5 min and resuspended as follows:

MDA-MB 231: 12,000 cells/ml of media;
MDA-MB 468: 25,000 cells/ml of media; and
MDA-MB 435: 12,000 cells/ml of media.

Cells were then plated into 48-well plates and incubated in accordance with suppliers' instructions. After 24 h media was removed and replaced with the following test media:

MDA-MB 468: 40 nM adriamycin;
MDA-MB 231: 50 nM adriamycin; and
MDA-MB 435: 10 nM adriamycin 40 nM Adriamycin media: 450 ml (Stock adriamycin is 1.7 mM, therefore 1,700,000/40=42,500; 450,000/42500=10.6 ul of 1.7 mM Adriamycin+450 ml Media).

Stock HA was 700,000 daltons at 14.3 µM HA

Conclusions

Figure 5:
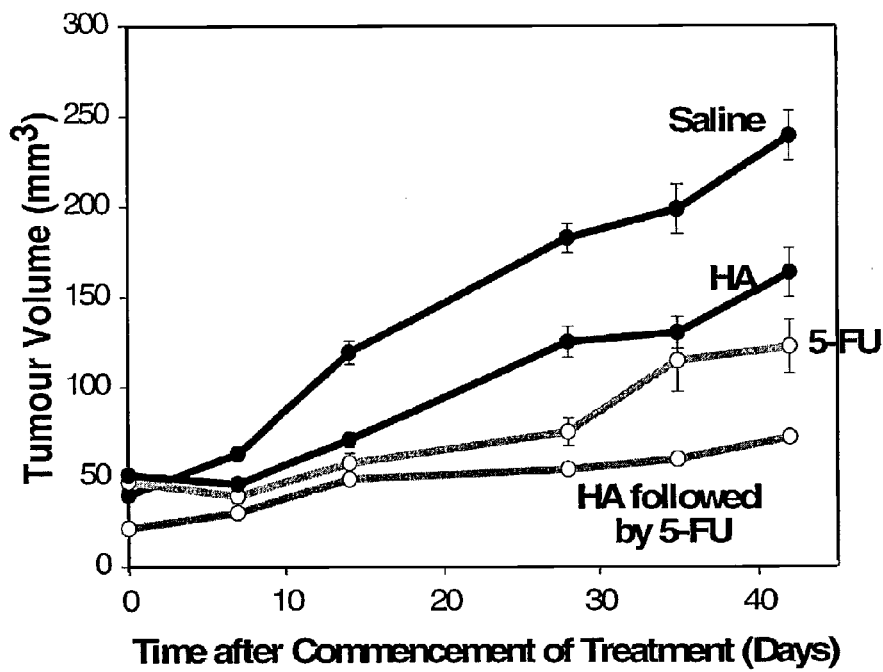
FIG. 5 shows that at the end of the 6 week study, tumour mass was determined where the HA chemosensitizing therapy had significantly smaller tumours than the saline group, HA and 5-FU groups (p=0.005). HA as a sole agent also demonstrated its effect by reducing the primary tumour mass in comparison to the saline control. No significant differences in tumour response were noted in the initial 2 weeks of treatment, but thereafter the HA followed by 5-FU tumour growth was retarded in comparison to the other treatment groups. During the 6 weeks of treatment interesting differences were noted in the number of tumour doubling cycles. Mice receiving the saline treatment underwent an average of 4 tumour doublings, while the incorporation of HA into the treatment regimen significantly increased the tumour doubling time where HA/5-FU animals underwent an average of one tumour doubling cycle, once again highlighting the effect of HA on 5-FU cytotoxicity.

This study has definitively proven that HA, can enhance the cytotoxicity of anti-cancer drugs, 5-FU and Adriamycin, both in vitro and in vivo. More specifically:

1). As a sole agent HA can exert a cytotoxic effect on cancer cells both in vitro and in vivo (FIG. 5);

2). Evaluation of the therapeutic efficacy of HA sole therapy or chemosensitizing therapy demonstrated that it was not toxic to normal tissue and it did not enhance the toxicity profile of the drug. In fact, mice receiving the therapy displayed a significant weight gain over the 6-week treatment period and a reduction in lymph node metastasis. The co-administration of HA and 5-FU had a dramatic effect on the reduction of the primary tumour volume; and 3) Mice who had HA incorporated into the treatment regimen did not display the formation of any secondary tumour (FIG. 6).

Future Studies

Experiments are presently being conducted on the use of HA for in vivo treatment of breast cancer. These experiments are focusing on the effect of HA concentration and molecular weight and on the cytotoxicity of adriamycin. It is the aim of these studies to also establishing drug and HA exposure time and regimens, as well as the mechanism of action of HA, ie: receptor mediated transport and/or effect on cell membrane. Further data on the role of HA in chemosensitizing drug-resistant cancer cells will also be collected.

Section 1:

All studies will be conducted on breast cancer cell lines that express differing levels of HA receptors, CD 44 and RHAMM. Cell lines to be tested, MDA-MB 435, MDA-MB 231, MDA-MB 468, ZRL-751 and several MDR-1 expressing breast cancer cell lines.

Investigation of the effect of HA/adriamycin exposure times and concentration on drug-resistant and drug-sensitive breast cancer cells. Four MDR-1 positive and 4 MDR-1 negative cell lines will be exposed to adriamycin at 1, 2.5, 5, 10, 20, 40, 60, 80 and 100 nM, the following variables will be tested:

1). 1 h drug±100 nM HA exposure followed by 3 days of drug-free growth;

2). Constant drug exposure±100 nM HA for 3 days 30 min 100 nM HA exposure, followed by drug for 1 h, cells grown drug-free for 3 days; and 3). 24 h 100 nM HA exposure, followed by drug for 1 h, cells grown drug-free for 3 days.

These experiments will establish; optimal HA exposure times and regimens, magnitude of increased adriamycin cytotoxicity when combined with HA and whether HA can overcome efflux pump resistance in breast cancer cells.

To date the $IC_{50}$ of adriamycin has been determined as 90 nM Using 90 nM of adriamycin the HA (700 kD) concentration will be varied to 1, 3, 10, 30, 100, 300 nM, 1 µM, 3 µM, 10 µM, 30 µM and 100 µM. The incubation variables to be tested are:

1). 30 min HA exposure followed by 1 h drug exposure cells grown drug-free for 3 days;

2). 24 HA exposure followed by 1 h drug exposure cells grown drug-free for 3 days; and 3). HA±drug exposure for 1 hr, cells grown drug-free for 3 days.

Any detached cells will be tested for cell viability since it has been suggested that HA can play a pivotal role in cancer cell detachment and migration. If detached cells are viable the HA receptor status will be determined using FACS surface epitope identification.

Similar experiments will be performed with short HA oligiosaccharides, ie: 4 sacc, 6 sacc, 12 sacc, 5600 Da, 50,000 Da, 100,000 Da, 250,000 Da.

These experiments will demonstrate the optimal HA:drug ratio in vitro, optimal HA exposure time and regimen, effect of HA molecular weight on adriamycin cytotoxicity.

After determining the optimal HA concentration, the $IC_{50}$ of adriamycin will be used in a series of time course experiments to observe any effect of HA on adriamycin metabolism.

The [$^{14}$C] adriamycin will be exposed to the cells for 30 min, 1 h, 2 h, 4 h, 8 h, 16 h and 24 h. The experimental conditions will be:

1). Exposure of cells to HA for 30 min followed by drug; and
2). Exposure of cells to HA for 24 followed by drug Co-exposure of HA/adriamycin.

Cells will be removed, hypotonically lysed and centrifuged at 113,000 gav for 1 hr. The membrane pellet and supernatant will be counted and analysed for metabolites using HPLC.

Cells will also be grown on coverslips, where they will be exposed to adriamycin±HA (exposures regimen as above) and a confocal photography time course will be used to track the cytosolic uptake and movement of the drug.

Identification of HA Receptors on MDR-1 positive and negative breast cancer cell lines, FACS quantitation of the CD44s, CD44v6, CD44v10 and RHAMM receptors will be conducted. Quantitation of the HA/receptor binding and saturation kinetics using FITC/HA and FACS analysis will also be done.

By exposing the cells to:
1). HA for 30 min followed by drug;
2). HA for 24 h followed by drug; and
3). HA/adriamycin We will be able to determine any of these block CD44s and RHAMM receptors. The receptor status of any viable cells will be quantitated using surface epitope FACS analysis. If blocking of the HA receptors decreases the normally observed synergism between adriamycin and HA, the membrane bound and cytosolic adriamycin will be quantited ±HA receptor blocking.

HA degradation by cell lines using [$^3$H]HA and gel filtration chromatography±receptor blocking will be studied.

HA of molecular weight, 4 sacc, 6 sacc, 12 sacc, 5600 Da, 50,000 Da, 100,000 Da, 250,000 Da, 750,000 Da and 1,500,000 Da will be incubated with breast cancer cell lines at pre-determined "observed-effect" concentrations and the following will be parameters investigated: Extracellular and intracellular calcium flux (cellular probe assays). Regulation of cytoskeletal components (micro-array of cytoskeletal genes), effect on volume of cells (Coulter size Analysis) and mobility of cancer cells (Boyden Chamber matrigel assays) will also be conducted.

The effect of HA on the cell cycle will be undertaken by incubating HA of molecular weight, 4 sacc, 6 sacc, 12 sacc, 5600 Da, 50,000 Da, 100,000 Da, 250,000 Da, 750,000 Da and 1,500,000 Da with breast cancer cell lines at pre-determined "observed-effect" concentrations. Cells will be labelled with potassium iodide and subjected FACS analysis. The number of cells in each stage of the cell cycle will be determined.

Comparisons of the in vitro efficacy of the liposomal Doxorubicin and HA/Doxorubicin preparations will be conducted using the optimal HA/Doxorubicin preparation and the dosage range used by the Liposome Company in the pre-clinical testing of the liposomal doxorubicin.

Section 2:

Before progression of the HA/adriamycin anti-cancer therapy into Phase I human breast cancer trials it is necessary to conduct preliminary toxicity experiments. The experiments will focus on:

1). Effect of hyaluronan on adriamycin uptake in mouse body organs and fluids;

2). Establish a preliminary dose range for adriamycin Determine if HA targets adriamycin to human breast tumour xenografts in nude mice;

3). Compare the commercial liposomal Doxorubicin to HA/doxorubicin uptake in mice; and 4) Comparison of short-term efficacy of liposomal doxorubicin and HA/doxorubicin.

From Inaba et al, (1988) the dose of adriamycin in nude mice was 4 mg/kg which is a human-equivalent dose of 60 mg/m$^2$. Nude mice bearing human tumours will be injected with adriamycin±HA. Using adraimycin concentrations of 4 mg/kg±12.5 mg/kg HA. The experimental protocol will include the following treatment groups:

1). 4 mg/kg adriamycin;
2). 4 mg/kg adriamycin+12.5 mg/kg HA; and
3). 4 mg/kg liposomal doxorubicin.

Using adriamycin±HA will be quantitatively injected into the tail vein of the mouse.

At the time intervals of 2, 15, 30, 60 min and 1.5, 2, 4, 8, 24 and 48 h (4 animals/time point) the mice will be killed by a 0.1 ml IP injection of Nembutal. All body organs, skeletal muscle, lymph nodes, bone marrow, urine and blood will be removed and the adriamycin content determined using HPLC and fluorescence.

Human breast tumours will be generated in nude mice (WEHI CBA strain) The mice will be injected with:

1). Mouse $LD_{50}$ is 10 mg/kg;
2). 4 mg/kg adriamycin;
3). 4 mg/kg adriamycin+12.5 mg/kg HA;
4). 8 mg/kg adriamycin;
5). 8 mg/kg adriamycin+12.5 mg/kg HA;
6). 4 mg/kg liposomal doxorubicin;
7). Saline; and
8). 12.5 mg/kg HA.

The above mentioned will be quantitatively injected into the tail vein of the mouse (8 animals/group) on Days 2, 4, 6 of a weekly cycle.

Tumour volume, body mass, food intake and functionality of the mice will be monitored on a daily basis.

At the completion of the 8-week study the mice will be killed by a 0.1 ml IP injection of Nembutal. All body organs, tumour, skeletal muscle, lymph nodes, bone marrow, urine and blood will be removed processed for pathological assessment.

Section 3:

To answer some basic questions about the effect of HA anti-cancer therapy on colon cancer cells the following experiments should be conducted.

Investigation of the effect of HA/5-FU exposure times and concentration on drug-resistant and drug-sensitive colon cancer cells.

Three resistant and 3 sensitive cell lines will be exposed to 5-FU at 1, 2.5, 5, 10, 20, 40, 60, 80 and 100 nM, the following variables will be tested:
1). 1 h drug±100 nM HA exposure followed by 3 days of drug-free growth;
2). Constant drug exposure±100 nM HA for 3 days;
3). 30 min 100 nM HA exposure, followed by drug for 1 h, cells grown drug-free for 3 days; and
4). 24 h 100 nM HA exposure, followed by drug for 1 h, cells grown drug-free for 3 days.

Using the $IC_{50}$ of 5-FU as determined as above, HA (700 kD) concentration will be varied to 1, 3, 10, 30, 100, 300 nM, 1 µM, 3 µM, 10 µM, 30 µM and 100 µM. The incubation variables to be tested:
1). 30 min HA exposure followed by 1 h drug exposure cells grown drug-free for 3 days;
2). 24 HA exposure followed by 1 h drug exposure cells grown drug-free for 3 days; and
3). HA±drug exposure for 1 hr, cells grown drug-free for 3 days.

Any detached cells will be tested for cell viability since it has been suggested that HA can play a pivotal role in cancer cell detachment and migration. If detached cells are viable the HA receptor status will be determined using FACS surface epitope identification.

Similar experiments will be performed with short HA oligiosaccharides, ie: 4 sacc, 6 sacc, 12 sacc, 5600 Da, 50,000 Da, 100,000 Da, 250,000 Da.

After determining the optimal HA concentration, the $IC_{50}$ of 5-FU will be used in a series of time course experiments to observe any effect of HA on adriamycin metabolism.

The [$^3$H] 5-FU will be exposed to the cells for 30 min, 1 h, 2 h, 4 h, 8 h, 16 h and 24 h. The experimental conditions will be:
1). Exposure of cells to HA for 30 min followed by drug; and
20. Exposure of cells to HA for 24 followed by drug Co-exposure of HA/5-FU.

Cells will be removed, hypotonically lysed and centrifuged at 113,000 gav for 1 hr. The membrane pellet and supernatant will be counted and analysed for metabolites using HPLC.

Cells will also be grown on coverslips, where they will be exposed to 5-FU±HA (exposures regimen as above) and a confocal photography time course will be used to track the cytosolic uptake and movement of the drug.

Identification of HA Receptors on resistant and sensitive colon cancer cell lines, FACS quantitation of the CD44s, CD44v6, CD44v10 and RHAMM receptors, Quantitation of HA/receptor binding and saturation kinetics using FITC/HA and FACS analysis will be done.

Blocking of CD44s and RHAMM receptors with inhibitory antibodies, apply 5-FU±HA following the protocols of:
1). Exposure of cells to HA for 30 min followed by drug; and
2). Exposure of cells to HA for 24 followed by drug co-exposure of HA/5-FU.

Cells will be counted. The receptor status of any viable cells will be quantitated using surface epitope FACS analysis.

If blocking of the HA receptors decreases the normally observed synergism between 5-FU and HA, the membrane bound and cytosolic 5-FU will be quantited ±HA receptor blocking.

HA degradation by cell lines using [$^3$H]HA and gel filtration chromatography±receptor blocking will be studied.

Effect of HA on the plasma membrane Hyaluronan of molecular weight, 4 sacc, 6 sacc, 12 sacc, 5600 Da, 50,000 Da, 100,000 Da, 250,000 Da, 750,000 Da and 1,500,000 Da will be incubated with breast cancer cell lines at pre-determined "observed-effect" concentrations and the following will be parameters investigated:
1). Extracellular and intracellular calcium flux (cellular probe assays);
2). Regulation of cytoskeletal components (micro-array of cytoskeletal genes);
3). Effect on volume of cells (Coulter size Analysis);
4). Mobility of cancer cells (Boyden Chamber matrigel assays);
5). Quantitation of HA receptors (FACS); and
6). Membrane potential (method to be determined).

An investigation of the role of HA neo-adjuvant therapy on the inhibition of organ metastasis will be undertaken. In comparison to other treatment groups, mice receiving the HA therapy have demonstrated that:
1). Reduced lymph node metastasis as compared to other treatment groups;
2). Inhibition of new tumour formation;
3). Increased weight gain; and
4). Enhanced well-being.

These results highlight the possible role of HA anti-cancer therapy as an efficient means of reducing the spread of cancer. Through the obligatory choice of a pre-clinical model there is a restriction, whereby the spread of the secondary cancer normally occurs in the surrounding lymph nodes. It would be advantageous to use a model where we can examine the spread of the cancer to every organ and the bone. By using a model known as the BAG vector metastasis model we would be able to monitor the spread of cancer to every organ and the bone.

In brief, the BAG vector consists of a neomycin-resistant LacZ gene that can be stably transfected into human breast cancer cells. After intracardiac injections into the nude mice, followed by a 6-week treatment program it is possible to PCR detect the LacZ gene in any metastasizing cells/organs. Faxitron scanning with detection of bone lesions would detect any bone metastasis.

The below treatments will be administered on Day 1, Day 2 of a weekly cycle, for 6 weeks. The treatment groups (5 animals per group) will consist of:
1. Saline
2. 30 mg/kg 5-FU Day 1, Day 2;
3. 12.5 mg/kg HA Day 1, Day 2;
4. 30 mg/kg 5-FU+12.5 mg/kg HA (co-administered on Day 1, Day 2);
5. 12.5 mg/kg HA on Day 1, 30 mg/kg 5-FU on Day 2, 12.5 mg/kg HA on Day 3, 30 mg/kg 5-FU on Day 4;
6. 12.5 mg/kg HA on Day 1, 3;
7. 30 mg/kg 5-FU on Day 2, 4;
8. 15 mg/kg MTX Day 1, Day 2;
9. 15 mg/kg MTX+12.5 mg/kg HA (co-administered on Day 1, Day 2);
10. 12.5 mg/kg HA on Day 1, 15 mg/kg MTX on Day 2, 12.5 mg/kg HA on Day 3, 15 mg/kg MTX on Day 4;
11. 15 mg/kg MTX on Day 2, Day 4;

12. 15 mg/kg MTX, 30 mg/kg 5-FU, 30 mg/kg cyclophosamide on Day 1, Day 2; and 13. 15 mg/kg MTX, 30 mg/kg 5-FU, 30 mg/kg cyclophosamide+12.5 mg/kg HA on Day 1, Day 2;

12.5 mg/kg HA on Day 1, (15 mg/kg MTX, 30 mg/kg 5-FU, 30 mg/kg cyclophosamide) on Day 2, 12.5 mg/kg HA on Day 3, (15 mg/kg MTX, 30 mg/kg 5-FU, 30 mg/kg cyclophosamide) on Day 4.

Neo-Adjuvant Therapy:

Immediately before intracardiac injection administer the following:

1). 12.5 mg/kg HA;
2). 15 mg/kg MTX;
3). 15 mg/kg MTX, 12.5 mg/kg HA;
4). 30 mg/kg 5-FU;
5). 30 mg/kg 5-FU, 12.5 mg/kg HA;
6). 15 mg/kg MTX, 30 mg/kg 5-FU, 30 mg/kg cyclophosamide; and
7). 15 mg/kg MTX, 30 mg/kg 5-FU, 30 mg/kg cyclophosamide+12.5 mg/kg HA.

Mouse mass and well being will be monitored daily for 6 weeks. On completion of the treatment cycle, each mouse will be scanned for bone lesions. After scanning each organ and body fluid will be removed. A sufficient cross section of the organ will be kept for possible future pathological analysis, while the remaining tissue will be homogenized and subjected to competitive PCR for the detection of the LacZ gene.

Any organs which exhibit metastasis will be histologically processed and the pattern of colonization of the cancer cells will be noted using galactosidase staining of the Lac Z gene.

REFERENCES

Culty, M., Shizari, M., Erik, W., Thompson. and Underhill, C. B. (1994). Binding and degradation of hyaluronan by human breast cancer cell lines expressing different forms of CD44: Correlation with invasive potential. *Journal of Cellular Physiology* 160: pp 275-286.

Culty, M., Nguyen, H A, and Underhill, C B. (1992). The hyaluronan receptor (CD44) participates in the uptake and degradation of hyaluronan. *J Cell Biol* 116 (4): pp 1055-1062.

Lang F., Ritter M., Volkl H and Haussinger D (1993). The biological Significance of cell volume Ren Physiol Biochem. 16: pp. 48-65.

Wang, C., Zhang, S. and Turley, E A. (1996). The role of hyaluronan and hyaluronan receptors in breast cancer cell invasion, motility and proliferation. In: Fourth International Workshop on Hyaluronan in Drug Delivery. (Editor: Willoughby, D. A) Roy. Soc. Med. Press. pp 37-53.

Wang, C., Tammi, M., Guo, H. and Tammi, R. (1997). Hyaluronan distribution in the normal epithelium of esophagus, stomach, and colon and their cancers. *American Journal of Pathology.* 148 (6): pp 1861-1869.

The claims defining the invention are as follows:

1. A method of treating drug resistant colon cancer comprising the step of systemically administering intravenously a composition comprising a combination of a therapeutically effective amount of hyaluronan, wherein the hyaluronan has a size expressed as a molecular weight of 800,000 to 1,432,000 Daltons or an intrinsic viscosity of 10.0 dl/gm to 14.5 dl/gm, together with a therapeutically effective amount of a cancer chemotherapeutic agent to a subject with drug resistant colon cancer.

2. A method according to claim 1, wherein the cancer chemotherapeutic agent is selected from the group consisting of carmustine (BCNU), chlorambucil (Leukeran), cisplatin (Platinol), Cytarabine, doxorubicin (Adriamycin), fluorouracil (5-FU), methoxetrate (Mexate), CPT-11 (irinotecan), etoposide, plicamycin (Mithracin) and taxanes.

3. A method according to claim 1 or 2, wherein the subject is mammal.

4. A method according to claim 3, wherein the mammal is selected from the group consisting of bovine, canine, equine, feline, porcine and human.

5. A method according to claim 1, wherein and the cancer chemotherapeutic agent is CPT-11 (irinotecan).

6. A method according to claim 1, wherein the hyaluronan is administered to the subject in an amount of between 5 mg per kilogram of body weight of the subject and 20 mg per kilogram of body weight of the subject.

7. A method according to claim 1, wherein the composition comprising hyaluronan and chemotherapeutic agent comprises less than 0.1% by weight protein content relative to hyaluronan.

8. A method according to claim 1, wherein the composition comprising hyaluronan and CPT-11 (irinotecan) comprises less than 0.1% by weight protein content relative to hyaluronan.

* * * * *

UNITED STATES PATENT AND TRADEMARK OFFICE
CERTIFICATE OF CORRECTION

Page 1 of 1

PATENT NO. : 8,388,993 B2
APPLICATION NO. : 11/415612
DATED : March 5, 2013
INVENTOR(S) : Tracey Brown It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1653 days.

Signed and Sealed this
Second Day of December, 2014

Michelle K. Lee
*Deputy Director of the United States Patent and Trademark Office*